US009085553B2

(12) United States Patent
Zeller et al.

(10) Patent No.: US 9,085,553 B2
(45) Date of Patent: Jul. 21, 2015

(54) LFA-1 INHIBITOR AND METHODS OF PREPARATION AND POLYMORPH THEREOF

(71) Applicant: SARcode Bioscience Inc., Brisbane, CA (US)

(72) Inventors: James Robert Zeller, Scottsdale, AZ (US); Sripathy Venkatraman, Slingerlands, NY (US); Elisabeth C. A. Brot, Albany, NY (US); Subashree Iyer, Guilderland, NY (US); Michael Hall, Albany, NY (US)

(73) Assignee: SARCODE BIOSCIENCE, INC., Brisbane, CA (US)

( * ) Notice: Subject to any disclaimer, the term of this patent is extended or adjusted under 35 U.S.C. 154(b) by 0 days.

(21) Appl. No.: 13/950,807

(22) Filed: Jul. 25, 2013

(65) Prior Publication Data
US 2014/0031387 A1    Jan. 30, 2014

Related U.S. Application Data

(60) Provisional application No. 61/675,663, filed on Jul. 25, 2012, provisional application No. 61/680,099, filed on Aug. 6, 2012, provisional application No. 61/729,294, filed on Nov. 21, 2012.

(51) Int. Cl.
    *C07D 405/06*    (2006.01)

(52) U.S. Cl.
    CPC .................................. *C07D 405/06* (2013.01)

(58) Field of Classification Search
    None
    See application file for complete search history.

(56) References Cited

U.S. PATENT DOCUMENTS

| | | |
|---|---|---|
| 3,773,919 A | 11/1973 | Boswell et al. |
| 4,668,506 A | 5/1987 | Bawa |
| 4,713,244 A | 12/1987 | Bawa |
| 4,767,628 A | 8/1988 | Hutchinson |
| 4,908,202 A | 3/1990 | Schulz |
| 4,931,279 A | 6/1990 | Bawa et al. |
| 4,992,445 A | 2/1991 | Lawter et al. |
| 5,001,139 A | 3/1991 | Lawter et al. |
| 5,023,252 A | 6/1991 | Hseih |
| 5,134,122 A | 7/1992 | Orsolini |
| 5,149,780 A | 9/1992 | Plow et al. |
| 5,192,741 A | 3/1993 | Orsolini et al. |
| 5,236,704 A | 8/1993 | Fujioka et al. |
| 5,288,854 A | 2/1994 | Diamond et al. |
| 5,298,492 A | 3/1994 | Neustadt et al. |
| 5,340,800 A | 8/1994 | Liu et al. |
| 5,397,791 A | 3/1995 | Hartman et al. |
| 5,424,289 A | 6/1995 | Yang et al. |
| 5,424,399 A | 6/1995 | Arnaout |
| 5,445,832 A | 8/1995 | Orsolini et al. |
| 5,470,953 A | 11/1995 | Gallatin et al. |
| 5,510,495 A | 4/1996 | Harris |
| 5,585,359 A | 12/1996 | Breslin et al. |
| 5,597,567 A | 1/1997 | Whitcup et al. |
| 5,612,052 A | 3/1997 | Shalaby |
| 5,622,700 A | 4/1997 | Jardieu et al. |
| 5,672,659 A | 9/1997 | Shalaby et al. |
| 5,747,035 A | 5/1998 | Presta et al. |
| 5,840,332 A | 11/1998 | Lerner et al. |
| 5,849,327 A | 12/1998 | Berliner et al. |
| 5,877,224 A | 3/1999 | Brocchini et al. |
| 5,893,985 A | 4/1999 | Luo et al. |
| 5,922,356 A | 7/1999 | Koseki et al. |
| 5,968,895 A | 10/1999 | Gefter et al. |
| 5,973,188 A | 10/1999 | Alig et al. |
| 5,980,945 A | 11/1999 | Ruiz |
| 6,180,608 B1 | 1/2001 | Gefter et al. |
| 6,204,280 B1 | 3/2001 | Gante et al. |
| 6,294,522 B1 | 9/2001 | Zablocki et al. |
| 6,331,640 B1 | 12/2001 | Fotouhi et al. |
| 6,340,679 B1 | 1/2002 | Peyman et al. |
| 6,358,976 B1 | 3/2002 | Wityak et al. |
| 6,515,124 B2 | 2/2003 | Fotouhi et al. |

(Continued)

FOREIGN PATENT DOCUMENTS

| | | |
|---|---|---|
| EP | 0314863 A2 | 5/1989 |
| EP | 0314863 A3 | 4/1990 |

(Continued)

OTHER PUBLICATIONS

Berge, et al. Pharmaceutical salts. J Pharmaceutical Sciences. 1977; 66: 1-19.
Boschelli, et al. 3-Alkoxybenzo[b]thiophene-2-carboxamides as inhibitors of neutrophil-endothelial cell adhesion. J Med Chem. 1994; 37(6): 717-8.
Boschelli, et al. Inhibition of E-Selectin-, ICAM-1-, and VCAM-1-mediated cell adhesion by benzo[b]thiophene-, benzufuran-, indole-, and naphthalene-2-carboxamides: Identification of PD 144795 as an antiinflammatory agent. J Med Chem. 1995; 38: 4597-614.
Burdick, et al. N-Benzoyl amino acids as ICAM/LFA-1 inhibitors. Part 2: Structure-activity relationship of the benzoyl moiety. Bioorganic & Medicinal Chemistry Letters. 2004; 14(9): 2055-9.

(Continued)

*Primary Examiner* — Zinna Northington Davis
(74) *Attorney, Agent, or Firm* — Troutman Sanders LLP

(57) ABSTRACT

Methods of preparation and purification of a compound of Formula I, intermediates thereof, a polymorph thereof, and related compounds are disclosed. Formulations and uses thereof in the treatment of LFA-1 mediated diseases are also disclosed.

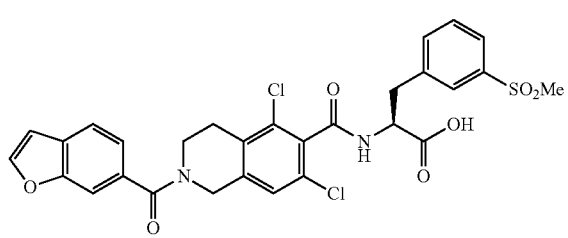

Formula I

16 Claims, 10 Drawing Sheets

(56) References Cited

U.S. PATENT DOCUMENTS

| | | |
|---|---|---|
| 6,524,581 B1 | 2/2003 | Adamis |
| 6,605,597 B1 | 8/2003 | Zablocki et al. |
| 6,620,422 B1 | 9/2003 | Maquin et al. |
| 6,642,225 B2 | 11/2003 | Albert et al. |
| 6,653,478 B2 | 11/2003 | Urbanski et al. |
| 6,667,060 B1 | 12/2003 | Vandecruys et al. |
| 6,667,318 B2 | 12/2003 | Burdick et al. |
| 6,670,321 B1 | 12/2003 | Adamis |
| 6,773,916 B1 | 8/2004 | Thiel et al. |
| 6,803,384 B2 | 10/2004 | Fotouhi et al. |
| 6,872,382 B1 | 3/2005 | Gamache et al. |
| 6,872,735 B2 | 3/2005 | Burdick et al. |
| 7,097,851 B1 | 8/2006 | Takada |
| 7,211,586 B2 | 5/2007 | Fenton et al. |
| 7,217,728 B2 | 5/2007 | Fotouhi et al. |
| 7,314,938 B2 | 1/2008 | Shen et al. |
| 7,785,578 B2 | 8/2010 | Miller et al. |
| 7,989,626 B2 | 8/2011 | Shen et al. |
| 8,080,562 B2 | 12/2011 | Burnier et al. |
| 8,084,047 B2 | 12/2011 | Shen et al. |
| 2001/0031260 A1 | 10/2001 | Lee et al. |
| 2002/0019446 A1 | 2/2002 | Brocchini et al. |
| 2002/0115692 A1 | 8/2002 | Archibald et al. |
| 2002/0119994 A1 | 8/2002 | Burdick et al. |
| 2002/0132807 A1 | 9/2002 | Wang et al. |
| 2002/0176841 A1 | 11/2002 | Barker et al. |
| 2002/0177591 A1 | 11/2002 | O'Donnell et al. |
| 2003/0044406 A1 | 3/2003 | Dingivan |
| 2003/0064105 A1 | 4/2003 | Kim et al. |
| 2003/0068320 A1 | 4/2003 | Dingivan |
| 2003/0068384 A1 | 4/2003 | Brocchini et al. |
| 2003/0138488 A1 | 7/2003 | Kohn et al. |
| 2003/0166630 A1 | 9/2003 | Auvin et al. |
| 2003/0171296 A1 | 9/2003 | Gefter et al. |
| 2003/0216307 A1 | 11/2003 | Kohn et al. |
| 2004/0006236 A1 | 1/2004 | Fotouhi et al. |
| 2004/0028648 A1 | 2/2004 | Adamis |
| 2004/0058968 A1 | 3/2004 | Burdick et al. |
| 2004/0120960 A1 | 6/2004 | Jardieu et al. |
| 2005/0080119 A1 | 4/2005 | Fotouhi et al. |
| 2005/0148588 A1 | 7/2005 | Burdick et al. |
| 2005/0267098 A1 | 12/2005 | Shen et al. |
| 2006/0281739 A1 | 12/2006 | Gadek et al. |
| 2007/0025990 A1 | 2/2007 | Dingivan |
| 2007/0155671 A1 | 7/2007 | Fotouhi et al. |
| 2008/0019977 A1 | 1/2008 | Adamis |
| 2008/0176896 A1 | 7/2008 | Shen et al. |
| 2008/0182839 A1 | 7/2008 | Shen et al. |
| 2009/0155176 A1 | 6/2009 | Burnier et al. |
| 2009/0298869 A1 | 12/2009 | Burnier et al. |
| 2010/0092541 A1 | 4/2010 | Burnier et al. |
| 2010/0092542 A1 | 4/2010 | Burnier et al. |
| 2011/0015394 A1 | 1/2011 | Rao et al. |
| 2011/0092707 A1 | 4/2011 | Burnier et al. |
| 2011/0124669 A1 | 5/2011 | Shen et al. |
| 2011/0165228 A1 | 7/2011 | Burnier et al. |
| 2011/0165229 A1 | 7/2011 | Burnier et al. |
| 2012/0107404 A1 | 5/2012 | Burnier et al. |
| 2012/0115858 A1 | 5/2012 | Tesconi et al. |
| 2012/0232019 A1 | 9/2012 | Gadek et al. |

FOREIGN PATENT DOCUMENTS

| | | |
|---|---|---|
| EP | 0362526 A2 | 4/1990 |
| EP | 0362531 A1 | 4/1990 |
| EP | 0362526 A3 | 7/1990 |
| EP | 0326151 B1 | 6/1993 |
| EP | 0656789 B1 | 12/1997 |
| EP | 0467389 B1 | 10/1999 |
| EP | 1392306 B1 | 1/2008 |
| JP | 4193895 | 7/1992 |
| WO | WO 90/03400 A1 | 4/1990 |
| WO | WO 90/10652 A1 | 9/1990 |
| WO | WO 90/13316 A1 | 11/1990 |
| WO | WO 91/19511 A1 | 12/1991 |
| WO | WO 92/03473 A1 | 3/1992 |
| WO | WO 93/16702 A1 | 9/1993 |
| WO | WO 93/24150 A1 | 12/1993 |
| WO | WO 94/03481 A1 | 2/1994 |
| WO | WO 94/11400 A1 | 5/1994 |
| WO | WO 94/15587 A2 | 7/1994 |
| WO | WO 94/15587 A3 | 9/1994 |
| WO | WO 95/04531 A1 | 2/1995 |
| WO | WO 95/28170 A1 | 10/1995 |
| WO | WO 96/09836 A1 | 4/1996 |
| WO | WO 97/04744 A1 | 2/1997 |
| WO | WO 97/26015 A1 | 7/1997 |
| WO | WO 97/40085 A2 | 10/1997 |
| WO | WO 97/40085 A3 | 1/1998 |
| WO | WO 98/13029 A1 | 4/1998 |
| WO | WO 98/25642 A2 | 6/1998 |
| WO | WO 98/25642 A3 | 7/1998 |
| WO | WO 98/46599 A1 | 10/1998 |
| WO | WO 99/49856 A2 | 10/1999 |
| WO | WO 99/49856 A3 | 11/1999 |
| WO | WO 00/21920 A1 | 4/2000 |
| WO | WO 00/38714 A1 | 7/2000 |
| WO | WO 00/44731 A1 | 8/2000 |
| WO | WO 01/01964 A2 | 1/2001 |
| WO | WO 01/12233 A2 | 2/2001 |
| WO | WO 01/27102 A1 | 4/2001 |
| WO | WO 01/01964 A3 | 6/2001 |
| WO | WO 01/49249 A2 | 7/2001 |
| WO | WO 01/49311 A1 | 7/2001 |
| WO | WO 01/58853 A1 | 8/2001 |
| WO | WO 01/12233 A3 | 11/2001 |
| WO | WO 01/87840 A1 | 11/2001 |
| WO | WO 01/49249 A3 | 1/2002 |
| WO | WO 02/30398 A2 | 4/2002 |
| WO | WO 02/38129 A2 | 5/2002 |
| WO | WO 02/50080 A1 | 6/2002 |
| WO | WO 02/058672 A2 | 8/2002 |
| WO | WO 02/059114 A1 | 8/2002 |
| WO | WO 02/074247 A2 | 9/2002 |
| WO | WO 02/058672 A3 | 12/2002 |
| WO | WO 02/074247 A3 | 12/2002 |
| WO | WO 02/098426 A1 | 12/2002 |
| WO | WO 02/38129 A3 | 2/2003 |
| WO | WO 02/30398 A3 | 3/2003 |
| WO | WO 03/053401 A2 | 7/2003 |
| WO | WO 03/075887 A1 | 9/2003 |
| WO | WO 03/053401 A3 | 1/2004 |
| WO | WO 2004/026406 A1 | 4/2004 |
| WO | WO 2005/014532 A1 | 2/2005 |
| WO | WO 2005/014533 A2 | 2/2005 |
| WO | WO 2005/014533 A3 | 4/2005 |
| WO | WO 2005/042710 A1 | 5/2005 |
| WO | WO 2005/044817 A1 | 5/2005 |
| WO | WO 2005/123706 A1 | 12/2005 |
| WO | WO 2006/125119 A1 | 11/2006 |
| WO | WO 2009/139817 A2 | 11/2009 |
| WO | WO 2009/139817 A3 | 1/2010 |

OTHER PUBLICATIONS

Burdick, et al. N-Benzoyl amino acids as LFA-1/ICAM inhibitors 1: amino acid structure-activity relationship. Bioorganic & Medicinal Chemistry Letters. 2004; 13(6): 1015-8.

Chang, et al. Effects of pharmacologic agents on the reversed passive Arthus reaction in the rat. Eur J Pharmacol. 1981; 69(2): 155-64.

Chavanpatil, et al. Novel sustained release, swellable and bioadhesive gastroretentive drug delivery system for ofloxacin. Int J Pharm. 2006; 316(1-2):86-92.

Coleman, et al. Chemoselective Cleavage of Benzyl Ethers, Esters, and Carbamates in the Presence of Other Easily Reducible Groups. Synthesis. 1999;1399-1400.

Cosimi, et al. In vivo effects of monoclonal antibody to ICAM-1 (CD54) in nonhuman primates with renal allografts. J Immunol. 1990; 144(12): 4604-12.

Crocker, et al. The role of fluorine substitution in the structure-activity relationships (SAR) of classical cannabinoids. Bioorg med chem lett. 2007; 17(6):1504-1507.

Davies et al. Physiological Parameters in Laboratory Animals and Humans. Pharmaceutical Research. 1993;10:1093-1095.

(56) References Cited

OTHER PUBLICATIONS

Diamond, et al. The dynamic regulation of integrin adhesiveness. Current Biology. 1994; 4(6): 506-32.
Earle et al. A Simplified Clinical Procedure for Measurement of Glomerular Filtration Rate and Renal Plasma Flow. Proc. Soc. Exp. Biol. Med.1946;62:262-269.
European office action dated Mar. 28, 2012 for Application No. 11181066.9.
European Office Action dated Nov. 9, 2010 for Application No. 6770607.7.
European office action dated Nov. 24, 2011 for Application No. 06770607.7.
European search report dated May 20, 2009 for Application No. 06770607.7.
Fischer, et al. Prevention of graft failure by an anti-HLFA-1 monoclonal antibody in HLA-mismatched bone-marrow transplantation. The Lancet. 1986; 2: 1058-60.
Fox. Systemic diseases associated with dry eye. Int Ophthalmol Clin, 1994 Winter, 34(1):71-87.
Frishberg, et al. Cyclosporine A regulates T cell-epithelial cell adhesion by altering LFA1- and ICAM-1 expression. Kidney Int. Jul. 1996;50(1):45-53.
Gadek, et al. Generation of an LFA-1 antagonist by the transfer of the ICAM-1 immunoregulatory epitope to a small molecule. Science. 2002; 295: 1086-9.
Gao, et al. ICAM-1 expression predisposes ocular tissues to immune-based inflammation in dry eye patients and Sjögrens syndrome-like MRL/lpr mice. Exp Eye Res. Apr. 2004;78(4):823-35.
Goodman, et al. Amino acid active esters. III. Base-catalyzed racemization of peptide active ester. Journal of Organic Chemistry, 1962; 27:3409-3416.
Gorski, A. The role of cell adhesion molecules in immunopathology. Immunology Today. 1994; 15: 251-5.
Hecht, et al. Effects of methyl and fluorine substitution on the metabolic activation and tumorigenicity of polycyclic aromatic hydrocarbons. ACS Symposium series. 1985; 283(5):85-105. Abstract only.
Higuchi, T., et al., "Pro-drugs as Novel Delivery Systems," A.C.S. Symposium Series, vol. 14, and in Bioreversible Carriers in Drug Design, ed. Edward B. Roche, American Pharmaceutical Association and Pergamon Press, 1987.
Hildreth, et al. Monoclonal antibodies against porcine LFA-1: Species cross-reactivity and functional effects of β-subunit-specific antibodies. Molecular Immunology. 1989; 26(9): 883-95.
Hoffman, et al. Pharmacokinetic and pharmacodynamic aspects of gastroretentive dosage forms. Int J Pharm. 2004; 277(1-2): 141-53.
Huang, et al. A binding interface of the I domain of lymphocyte function-associated antigen-1 (LFA-1) required for specific interaction with intercellular adhesion molecule 1 (ICAM-1). J Biological Chemistry. 1995; 270(32): 19008-16.
International search report and written opinion dated Dec. 22, 2010 for PCT Application No. US10/53571.
International search report and written opinion dated Sep. 24, 2009 for PCT Application No. US2009/02391.
International search report dated Sep. 19, 2006 for PCT Application No. PCT/US2006/19327.
International Search Report and Written Opinion of the International Searching Authority dated Dec. 30, 2013, from corresponding International Application No. PCT/US13/52044.
Kaiser, et al. Hydrolysis-induced racemization of amino acids. Limnol. Oceanogr. Methods. 2005; 3:318-325.
Kavanaugh, et al. Treatment of refractory rheumatoid arthritis with a monoclonal antibody to intercellular adhesion molecule 1. Arthritis Rheum. 1994; 37(7): 992-1004.
Keating, et al. Competition between intercellular adhesion molecule-1 and a small-molecule antagonist for a common binding site on the alpha1 subunit of lymphocyte function-associated antigen-1. Protein Sci. 2006; 15(2):290-303.
Keating, et al. Putting the pieces together: Contribution of fluorescence polarization assays to small molecule lead optimization. Proc. SPIE. 2000; vol. 3913, p. 128-137. (Online Publication Date: Jul. 2, 2003).
Kishimoto, et al. Integrins, ICAMs, and selectins: Role and regulation of adhesion molecules in neutrophil recruitment to inflammatory sites. Adv Pharmacol. 1994; 25: 117-69.
Klausner, et al. Novel gastroretentive dosage forms: evaluation of gastroretentivity and its effect on levodopa absorption in humans. Pharm Res. 2003; 20(9): 1466-73.
Kunert, et al. Analysis of Topical Cyclosporine Treatment of Patients with Dry Eye Syndrome. Arch Ophthalmol, vol. 118, Nov 2000, 1489-1496.
Kunert, et al. Goblet cell numbers and epithelial proliferation in the conjunctiva of patients with dry eye syndrome treated with cyclosporine. Arch Ophthalmol. Mar. 2002;120(3):330-7.
Le Mauff, et al. Effect of anti-LFA1 (CD11a) monoclonal antibodies in acute rejection of human kidney transplantation. Transplantation. 1991; 52(2): 291-5.
Legarreta Eye Center, Dry Eye, Jan 2002, printed from http://www.legarretaeyecenter.com/dry-eye.html with Google date entry, 3 pages.
Ley, et al. Getting to the site of inflammation: the leukocyte adhesion cascade updated. Nat Rev Immunol. Sep. 2007;7(9):678-689.
Liu, G. Inhibitors of LFA-1/ICAM-1 interaction: from monoclonal antibodies to small molecules. Drugs of the Future. 2001; 26: 767-78.
Liu, G. Small molecule antagonists of the LFA-1/ICAM-1 interaction as potential therapeutic agents. Expert Opin Ther Patents. 2001; 11: 1383-93.
Lu, et al. The binding sites for competitive antagonistic, allosteric antagonistic, and agonistic antibodies to the I domain of the integrin LFA-1. J Immunol. 2004; 173: 3972-8.
Murphy, et al. The Pharmacologic Assessment of a Novel Lymphocyte Function-Associated Antigen-1 Antagonist (SAR 1118) for the Treatment of Keratoconjunctivitis Sicca in Dogs. Invest Ophthalmol Vis Sci. May 16, 2011;52(6):3174-80.
Musza, et al. Potent new cell adhesion inhibitory compounds from the root of Trichilia rubra. Tetrahedron. 1994; 50(39): 11369-78.
Office action dated Jun. 7, 2011 for U.S. Appl. No. 11/436,906.
Office Action dated Jun. 8, 2011 for U.S. Appl. No. 12/508,367.
Office action dated Sep. 8, 2011 for U.S. Appl. No. 12/386,361.
Office action dated Sep. 15, 2011 for U.S. Appl. No. 13/011,760.
Office Action dated Sep. 28, 2010 for U.S. Appl. No. 12/508,311.
Office Action dated Sep. 28, 2010 for U.S. Appl. No. 12/508,367.
Office action dated Oct. 5, 2011 for U.S. Appl. No. 13/011,775.
Office action dated Nov. 9, 2012 for U.S. Appl. No. 13/289,172.
Office Action dated Dec. 21, 2010 for U.S. Appl. No. 11/436,906.
Park, et al. Effects of fluorine substitution on drug metabolism: pharmacological and toxicological implications. Drug Metab Rev. 1994;26(3):605-43.
Park, et al. Metabolism of fluorine-containing drugs. Annu Rev Pharmacol Toxicol. 2001;41:443-70.
Patani, et al. Bioisosterism: A rational approach in drug design. Chem. Rev. 1996; 96:3147-3176.
Plobeck, et al. New diarylmethylpiperazines as potent and selective nonpeptidic δ opioid receptor agonists with increased in vitro metabolic stability. J Med Chem. 2000; 43: 3878-94.
Rothlein, et al. 1. Leukocyte adhesion in inflammation: From discovery to the clinic. Adhesion Molecules. Wegner, C.D., Ed.; 1994: 1-8.
Salas, et al. Rolling adhesion through an extended conformation of integrin αLβ2 and relation to α I and B I-like domain interaction. Immunity. 2004; 20(4): 393-406.
Sanfilippo, et al. Novel thiazole based heterocycles as inhibitors of LFA-1/ICAM-1 mediated cell adhesion. J Med Chem. 1995; 38: 1057-9.
Sapirstein et al. Volumes of Distribution and Clearances of Intravenously Injected Creatinine in the Dog. *American Journal of Physiology.* 1955;181:330-336.

(56) References Cited

OTHER PUBLICATIONS

Shimaoka, et al. Reversibly locking a protein fold in an active conformation with a disulfide bond: Integrin alpha L I domains with high affinity and antagonist activity in vivo. PNAS. 2001; 98(11): 6009-14.

Shimaoka, et al. Small molecule integrin antagonists that bind to the β2 subunit Ilike domain and activate signals in one direction and block them in the other. Immunity. 2003; 19(3): 391-402.

Shimaoka, et al. Structures of the αL I domain and its complex with ICAM-1 reveal a shape-shifting pathway for integrin regulation. Cell. 2003; 112(1): 99-111.

Shimaoka, et al. Therapeutic antagonists and the conformational regulation of the B2 integrins. Curr Topics Med Chem. 2004; 4: 1485-95.

Shulman, et al. Lymphocyte crawling and transendothelial migration require chemokine triggering of high-affinity LFA-1 integrin. Immunity. Mar. 20, 2009;30(3):384-396.

Solomans. Fundamentals of Organic Chemistry. 5th ed. 1982; 630.

Springer, T. Adhesion receptors of the immune system. Nature. 1990; 346: 425-34.

Stern, et al. Conjunctival T-cell subpopulations in Sjögren's and non-Sjögren's patients with dry eye. Invest Ophthalmol Vis Sci. Aug. 2002;43(8):2609-14.

Streubel, et al. Gastroretentive drug delivery systems. Expert Opin Drug Deliv. 2006; 3(2): 217-33.

*The Eye Digest*, Eye Exam for Dry Eyes, Mar. 2003, printed from http://www.agingeye.net/dryeyes/dryeeyeseyeexam.php and google date entry, 4 pages.

Ward, S. Millipede-like lymphocyte crawling: feeling the way with filopodia. Immunity. Mar. 20, 2009;30(3):315-317.

Welzenbach, et al. Small molecule inhibitors induce conformational changes in the I domain and the I-like domain of lymphocyte function-associated antigen-1. J Biological Chemistry. 2002; 277(12): 10590-8.

Wermuth. The practice of medicinal chemistry-molecular variations based on isosteric replacements. Academic Press Limited. 1996; 226-228.

Zhong, et al. Discovery and Development of Potent LFA-1/ICAM-1 Antagonist SAR 1118 as an Ophthalmic Solution for Treating Dry Eye. ACS Med. Chem. Lett. DOI: 10.1021/ml2002482. Publication Date (Web): Jan. 31, 2012.

| Form | Alternate Name | Isolation | XRPD | ¹HNMR wt% Residual Solvent | DSC (°C) | TGA loss (wt%) | Moisture Sorption | Threshold Solubility in Na₂HPO₄ PH =7.2 |
|---|---|---|---|---|---|---|---|---|
| I (Channel Hydrate) | A | Aqueous actone | Cryst | Consistent w/Structure | 163.3 | 1.0% Decomp. 258.9°C | 60% RH: 1.2 wt% 90% RH: 1.3 wt% | 6.7 wt% |
| II | — | Acetone/n-heptane | Cryst | 0.2 wt% acetone | 38, 156 | 1.5% Decomp. 260.3°C | 60% RH: 3.0 wt% 90% RH: 3.4 wt% | ND |
| III (Monohydrate) | E | — | Cryst | MEK = 1.1 wt% | 69.2 157.3 | 1.4% between 40 – 90 °C 1.0% between 110 – 160 °C Decomp 252.6 °C | 60% RH: 3.6 wt% 90% RH: 6.2 wt% | 5 wt% |
| IV (Monohydrate) | C | IPA slurry | Cryst | IPA = - 0.1 wt% | 57.5 143.0 165.5 | 1.3% between 40 – 60 °C 1.5% between 110 – 150 °C Decomp. 257.0 °C | 60% RH: 2.7 wt% 90% RH: 4.2 wt% | ND |
| V (Anhydrate) | B | EtOAc slurry | Cryst | EtOAc = 0.3 wt% | 208.5 | No Weight Loss Decomp 266.3 °C | 60% RH: 0.06 wt% 90% RH: 0.12 wt% | ND |
| VI (Hydrate) | D | Acetone/H₂O slurry | Cryst | ND | 79.8 151.2 | 3.5% between 20-140 °C Decomp. 249.1 °C | ND | 5 wt% |
| Amorphous | Amorphous | MIBK/Toluene | Amorph | MIBK – 3.8 wt% | Tg= 82.4 | 3.3% between 70 – 160 °C Decomp. 228.1 °C | 60% RH: 1.2 wt% 90% RH: 3.1 wt% | ND |

(–) = Not identified
^ = exotherm
ND = Not determined

Fig. 10

LFA-1 INHIBITOR AND METHODS OF PREPARATION AND POLYMORPH THEREOF

CROSS-REFERENCE TO RELATED APPLICATIONS

This application claims priority from U.S. Provisional Application Ser. No. 61/675,663, filed Jul. 25, 2012, U.S. Provisional Application Ser. No. 61/680,099, filed Aug. 6, 2012, and U.S. Provisional Application Ser. No. 61/729,294, filed Nov. 21, 2012, the disclosures of which are hereby incorporated by reference in their entireties.

BACKGROUND OF THE INVENTION

The compound of Formula I:

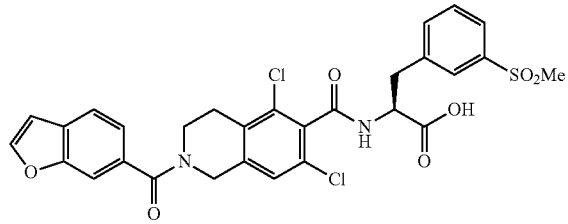

Formula I has been found to be an effective inhibitor of Lymphocyte Function-Associated Antigen-1 (LFA-1) interactions with the family of Intercellular Adhesion Molecules (ICAM), and has desirable pharmacokinetic properties, including rapid systemic clearance. However, improved methods of preparation are useful for providing the compound of Formula I with increased purity and/or with reduced use of starting materials.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10 is a characterization summary of the Forms of Formula I.

SUMMARY OF THE INVENTION

Figure 1:
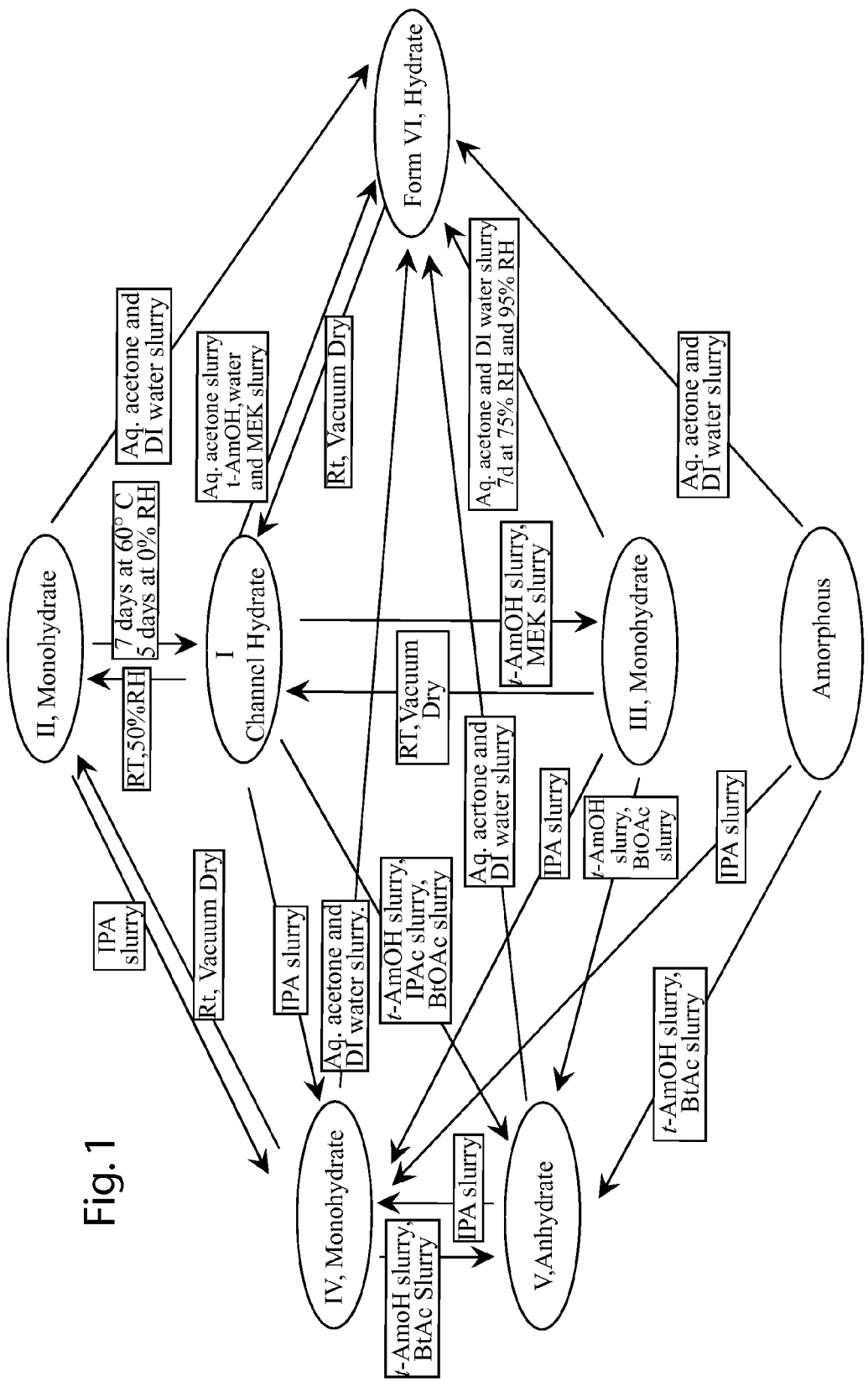
FIG. 1 is a flow diagram showing correlation between different Forms of Formula I.
Figure 2:
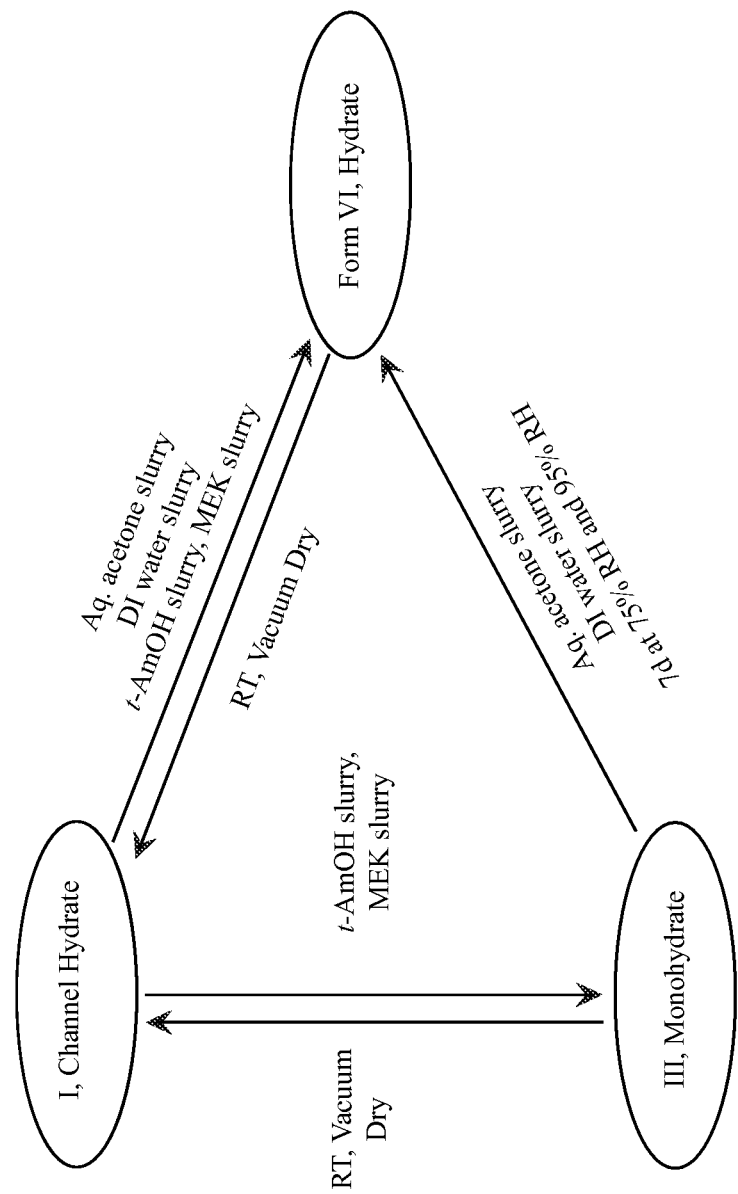
FIG. 2 is a flow diagram showing inter-conversion between Forms I, III and VI of Formula I.
Figure 3:
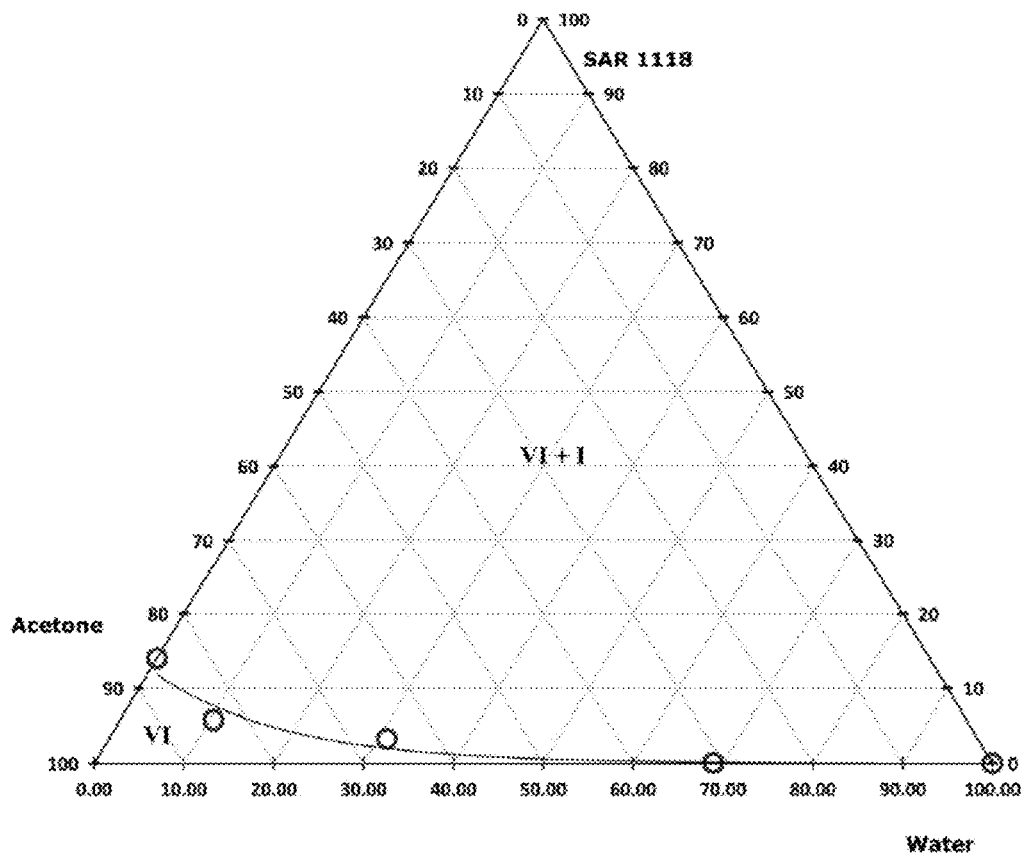
FIG. 3 is a ternary phase diagram of Formula I in an aqueous acetone system.

In a first aspect, the invention provides methods of making a compound of Formula I:

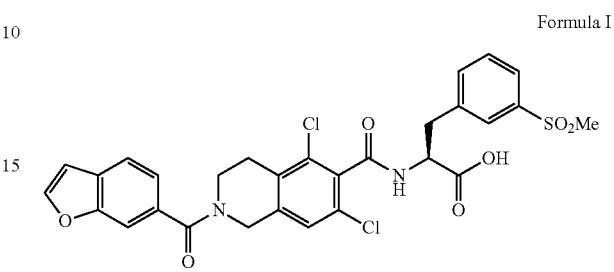

Formula I or a salt thereof. According to the invention, such methods comprise the steps of performing hydrolysis of a precursor ester with a base under biphasic conditions where the precursor ester group is a carbon-containing moiety or a silyl-containing moiety; and b) isolating the compound of Formula I or a salt thereof. In various embodiments, the biphasic conditions include aqueous acetone, such as 30% aqueous acetone. In various embodiments, the biphasic conditions change over time such that a reaction mixture that is biphasic at initiation of reaction becomes less biphasic or monophasic as the reaction proceeds.

In various embodiments, the base for hydrolysis is sodium hydroxide, for example, in amounts ranging from about 1.0 to about 1.5 equivalents, preferably about 1.2 equivalents.

In various embodiments, the precursor ester includes an ester R group which is a substituted or unsubstituted group selected from lower alkyl, lower alkenyl, lower alkynyl, cyclo(lower)alkyl, cyclo(lower)alkenyl, aryl, aralkyl, heterocyclyl, and heteroaryl groups. Preferably, the ester R group is a benzyl group.

In various embodiments, the invention provides methods of making a compound of Formula I requiring the use of a phase transfer catalyst for performing base-catalyzed hydrolysis. In various embodiments, the phase transfer catalyst is a quaternary ammonium salt such as tetrabutylammonium hydroxide. Such phase transfer catalysts may be present in an amount ranging from about 0.01 equivalents to about 0.5 equivalents.

In a second aspect, the invention provides compositions which are reaction mixtures corresponding to the methods of making the compound of Formula I as described above.

In a third aspect, the invention provides methods of purifying a compound of Formula I by recrystallization. In various embodiments, the recrystallization is performed with aqueous acetone. Accordingly, methods are provided comprising a) obtaining crude compound of Formula I or a salt thereof and recrystallizing the crude compound with aqueous acetone; and b) isolating the compound of Formula I or a salt thereof by removal of aqueous acetone. Preferably, the aqueous acetone is about 30% aqueous acetone. In various embodiments, the aqueous acetone is used in an amount of about 7 volumes. Preferably, the method is performed for a period of time ranging from about 1 hour to about 48 hours.

In a fourth aspect, the invention provides compositions which are recrystallization mixtures corresponding to the methods of purifying a compound of Formula I as described above.

In a fifth aspect, the invention provides a compound of Formula I synthesized according to the methods described herein, or recrystallized according to the methods described herein, or both. Preferably, the compound is essentially free of methyl ethyl ketone. In various embodiments, the compound of Formula I has an enantiomeric excess of greater than about 96% upon isolation from the reaction mixture for base-catalyzed hydrolysis and prior to recrystallization. In various embodiments, the compound of Formula I synthesized and/or recrystallized according to the methods of the invention has an enantiomeric excess of greater than about 98%.

In a sixth aspect, the invention provides a compound of Formula I wherein the compound is polymorph Form II as described herein. In various embodiments, the compound polymorph Form II is present in a solid composition with a pharmaceutically acceptable carrier. In various embodiments, the composition is at least about 50% by weight Form II, or alternatively, less than about 5% by weight Form II. In various embodiments, the solid composition further comprises one or more solid forms selected from the group consisting of amorphous, Form I, Form III, Form IV, Form V, and Form VI.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While selected embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

As used herein, the term "pharmaceutically acceptable salt" refers to those salts which are suitable for pharmaceutical use, preferably for use in the tissues of humans and lower animals without undue irritation, allergic response and the like. Pharmaceutically acceptable salts of amines, carboxylic acids, and other types of compounds, are well known in the art. For example, S. M. Berge, et al., describe pharmaceutically acceptable salts in detail in J Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed by direct reaction with the drug carboxylic acid or by using counterions such as halide, hydroxide, carboxylate, sulfate, phosphate, nitrate, sulfonate and aryl sulfonate.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, i.e. an ester, but is converted in vivo to an active compound, for example, by hydrolysis to the free carboxylic acid. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

"Subject" refers to an animal, such as a mammal, for example a human. The methods described herein can be useful in both human therapeutics and veterinary applications. In some embodiments, the patient is a mammal, and in some embodiments, the patient is human. In various embodiments, the patient is a non-human animal, such as a dog, cat, rabbit, mouse, rat, cow, horse, pig, or chicken.

Unless otherwise stated, structures depicted herein are also meant to include compounds which differ only in the presence of one or more isotopically enriched atoms. For example, compounds having structures wherein a hydrogen is replaced by by a deuterium or tritium, or a carbon is replaced by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

Abbreviations used herein have their conventional meaning within the chemical and biological arts.

Compound of Formula I

The compound of Formula I:

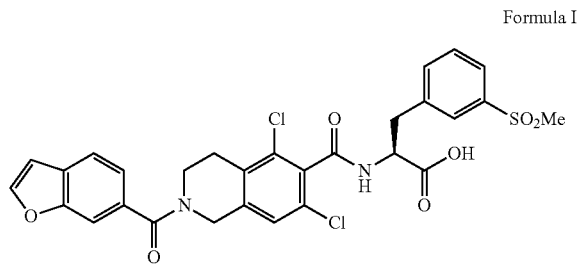 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula I has been found to be an effective inhibitor of LFA-1 interactions with ICAM-1. It is a member of a class of directly competitive inhibitors of LFA-1, binding to ICAM's binding site on LFA-1 directly, and thus excludes ICAM binding. Directly competitive inhibitors of LFA-1 may offer the potential for more effective modulation of the inflammatory and/or immunologic response than allosteric inhibitors provide because these inhibitors occlude the binding site more effectively. Pharmaceutically acceptable salts of Formula I are also included. Additional information regarding the compound of Formula I can be found in U.S. Pat. No. 8,080,562; US Patent Publication 2009/0298869; US Patent Publication 2011/0092707; U.S. Pat. No. 8,084,047; US 2010/0092542; and US Patent Publication 2006/0281739; the entire contents of each of which are incorporated by reference.

In order to develop clinically useful therapeutics, drug candidates need to be chemically pure enough to administer to a subject and of an acceptable physical form in order to be formulated in pharmaceutically acceptable dosage forms. One advantageous route to obtain higher purity, reproducibility of physical form, and stability is to identify one or more useful crystalline forms. The capacity to exist in different crystalline forms is known as polymorphism and is known to occur in many organic molecules. These different crystalline forms are known as "polymorphic modifications" or "polymorphs." While polymorphic modifications have the same chemical composition, they differ in packing, geometric arrangement, and other descriptive properties of the crystalline solid state. As such, these modifications may have different solid-state physical properties to affect, for example, the solubility, dissolution rate, bioavailability, chemical and physical stability, flowability, fractability, and compressibility of the compound as well as the safety and efficacy of drug products based on the compound. In the process of preparing a polymorph, further purification, in terms of gross physical purity or optical purity, may be accomplished as well.

A number of different forms, including crystalline forms, of the compound of Formula I have been discovered, including the crystalline forms A-E and the amorphous form. While crystallization is often performed on organic compounds, it is not predictable in advance as to which conditions will provide suitable conditions to lead to formation of a particular crystalline form. Further, it is not predictable as to which particular crystalline form will provide the necessary mixture of physical properties, nonlimiting examples of which are described above, to yield a desirable drug dosage form, once formulated. Additional information regarding the crystalline forms A-E and the amorphous form of the compound of Formula I can be found in U.S. Pat. No. 8,080,562; US Patent Publication 2009/0298869; US Patent Publication 2011/0092707; U.S. Pat. No. 8,084,047; US 2010/0092542; and US Patent Publication 2006/0281739; the entire contents of each of which are incorporated by reference.

Methods of Manufacture of the Compound of Formula I

In one embodiment, the compound of Formula I is synthesized as in the following Schemes 1-7. The final product of this synthesis yields the compound of Formula I as an amorphous solid or as a crystalline form such as Forms A-E, or a pharmaceutically acceptable salt, either directly or indirectly. Variants of this overall route may provide superior yields, cost of goods, and/or superior chiral purity.

Protecting groups for amino and carboxy groups are known in the art. For example, see Greene, Protective Groups in Organic Synthesis, Wiley Interscience, 1981, and subsequent editions.

In various embodiments in the subsequent schemes, HATU is used as a reagent in amide-bond forming reactions. Alternatively, HATU is not used. In various embodiments, at least one amide-bond forming reaction is performed with thionyl chloride as a reagent in place of HATU. In various embodiments, all amide-bond forming reactions are performed with thionyl chloride as a reagent to form acid chlorides.

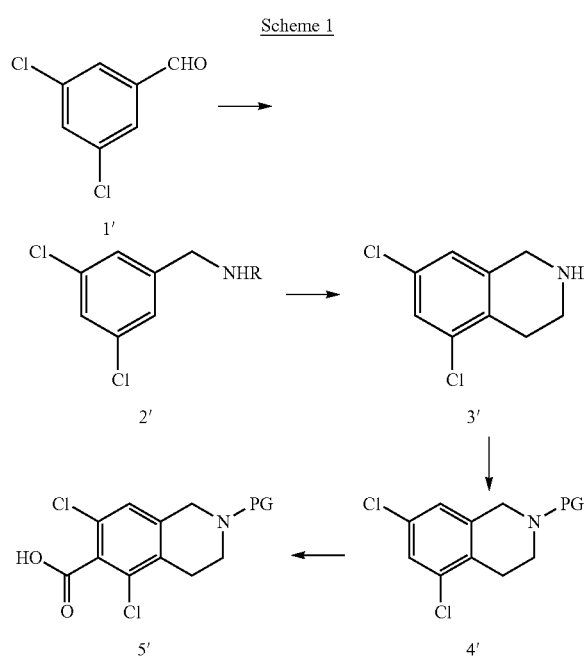

Scheme 1

A first alternative protecting strategy produces compound 5', a protected species as shown in Scheme 1. The synthesis begins by reductively aminating 3, 5, dichlorobenzaldehyde, compound 1'. Cyclization of compound 2' provides compound 3'. Protection of the free amine of compound 3' as a protected species provides compound 4'. A carboxylic acid functionality is introduced by treatment of compound 4' with introduction of carbon dioxide, to produce compound 5'. In various embodiments, the protecting group of compound 4' is a benzofuranyl carbonyl moiety derived from compound 18'.

In various embodiments, upon scaleup to multikilogram and larger scale reactions, treatment of compound 4' with strong base (such as n-butyllithium (nBuLi) to generate a lithio species, or lithium diisopropyl amide (LDA) to generate the lithio species) is performed in flow mode rather than batchwise reaction due to instability of lithio species except at cold temperatures. Flow rates and residence times may be adjusted to maximize yield.

In various embodiments, 6-hydroxy-1,2,3,4-tetrahydroisoquinoline (Compound 3'') is used as a starting material for Compound 5'. The starting material is chlorinated (x2) for example, with N-chlorosuccinimide. In various embodiments, the chlorination is performed in the presence of a sulfonic acid. In various embodiments, the sulfonic acid is selected from p-toluenesulfonic acid and methanesulfonic acid. Following protection of the amino group, the hydroxy group is functionalized, for example, as the triflate ester, which is carbonylated to yield the amino-protected methyl ester. Hydrolysis of the methyl ester yields the amino protected carboxylic acid.

In various embodiments, bromophenylalanine is used as the starting material for a portion of the final molecule as shown in Scheme 2. The starting material is protected with an amino protecting group to allow for introduction of a methyl sulfone functionality in compound 8'. Protecting groups are rearranged by introduction of an orthogonal protecting group for the carboxylic moiety, followed by deprotection of the amino group to provide compound 10'. In various embodiments, expensive or exotic bases are replaced with carbonate base such as potassium carbonate or calcium carbonate as a reagent.

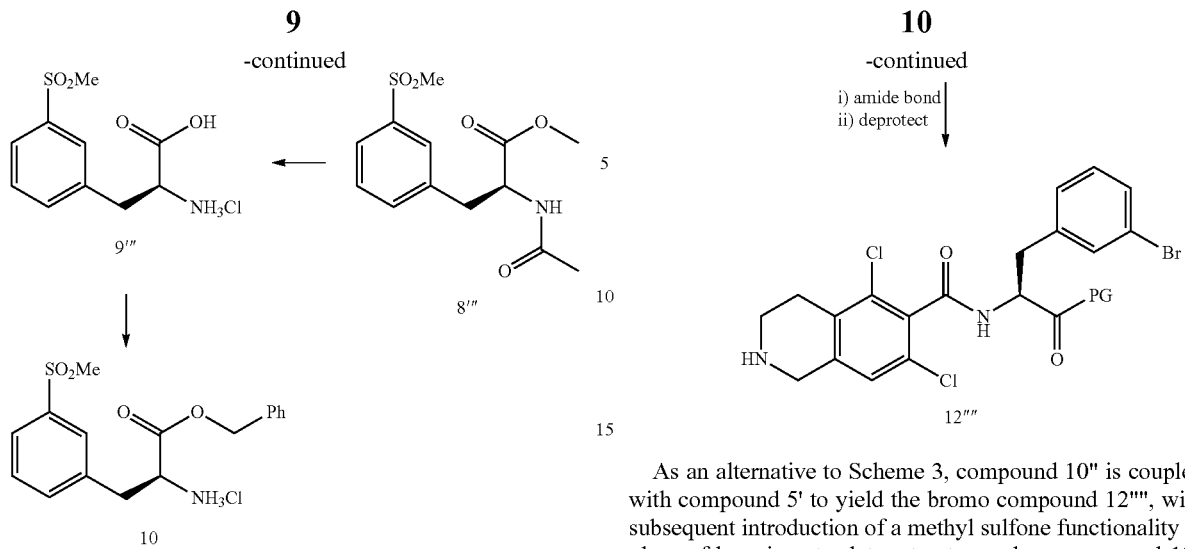

In various embodiments, 3-methylsulfonylbenzaldehyde is converted into the 3-methylsulfonylphenylalanine derivative and functionalized to yield compound 10 as shown above.

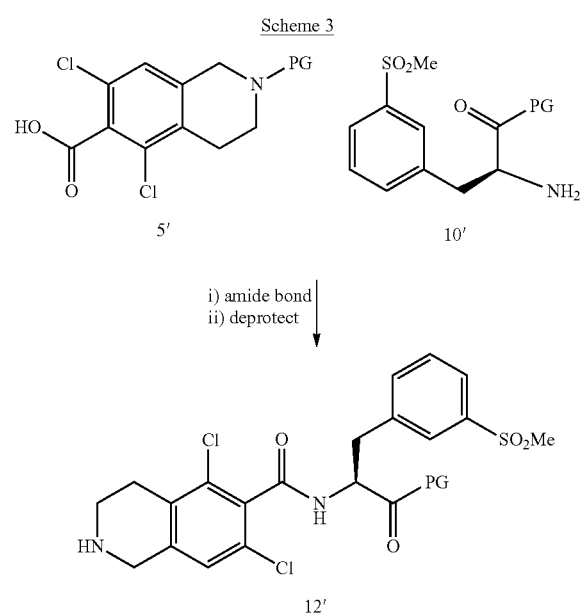

Compounds 5' and 10' are joined through amide bond formation followed by deprotection of the remaining amino group in the presence of the carboxylic protecting group to yield compound 12' or a salt thereof, such as the HCL salt.

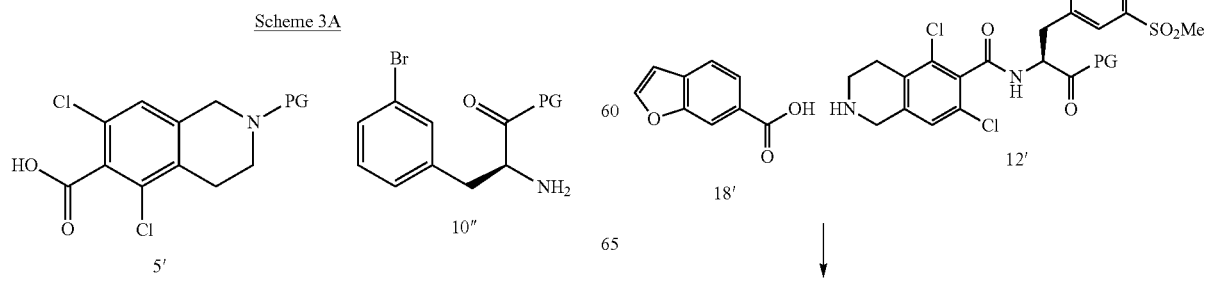

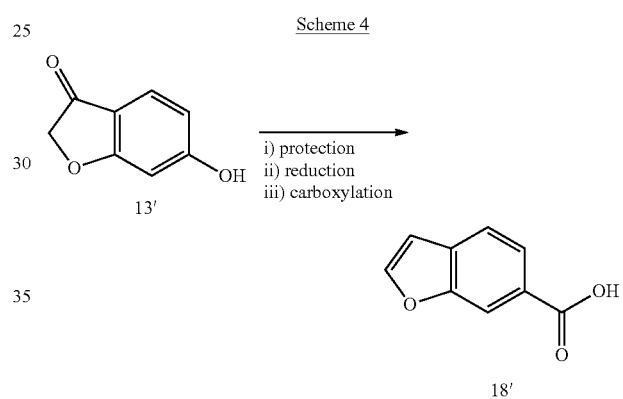

As an alternative to Scheme 3, compound 10" is coupled with compound 5' to yield the bromo compound 12"", with subsequent introduction of a methyl sulfone functionality in place of bromine at a later step to produce compound 19'. Alternatively, instead of a bromine, compound 10" includes X, where X is any halide (Cl, I, Br, F) or a leaving group such as OTs, OTf, or the like.

Scheme 4

The benzofuranyl carbonyl moiety of the compound of Formula I can be prepared using various alternative schemes. In one embodiment, the benzofuranyl carbonyl moiety is prepared by protecting the hydroxyl group of compound 13', reducing the carbonyl of compound 13' to yield the benzofuranyl moiety, followed by carboxylation to yield compound 18'.

In one embodiment, compound 18' is prepared from 6-hydroxybenzofuran via the triflate ester and the 6-carboxy methyl ester as intermediates, as shown in Example 4A.

Scheme 5

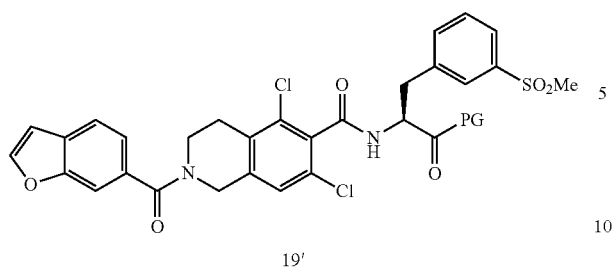
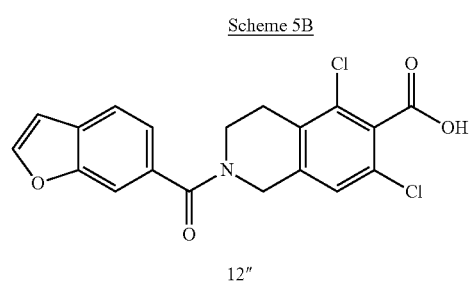

The benzofuran carboxylic acid 18' is coupled with compound 12' (or a salt thereof) by amide bond formation to yield protected compound 19', as shown in Scheme 5. Amide bond formation is known in the art

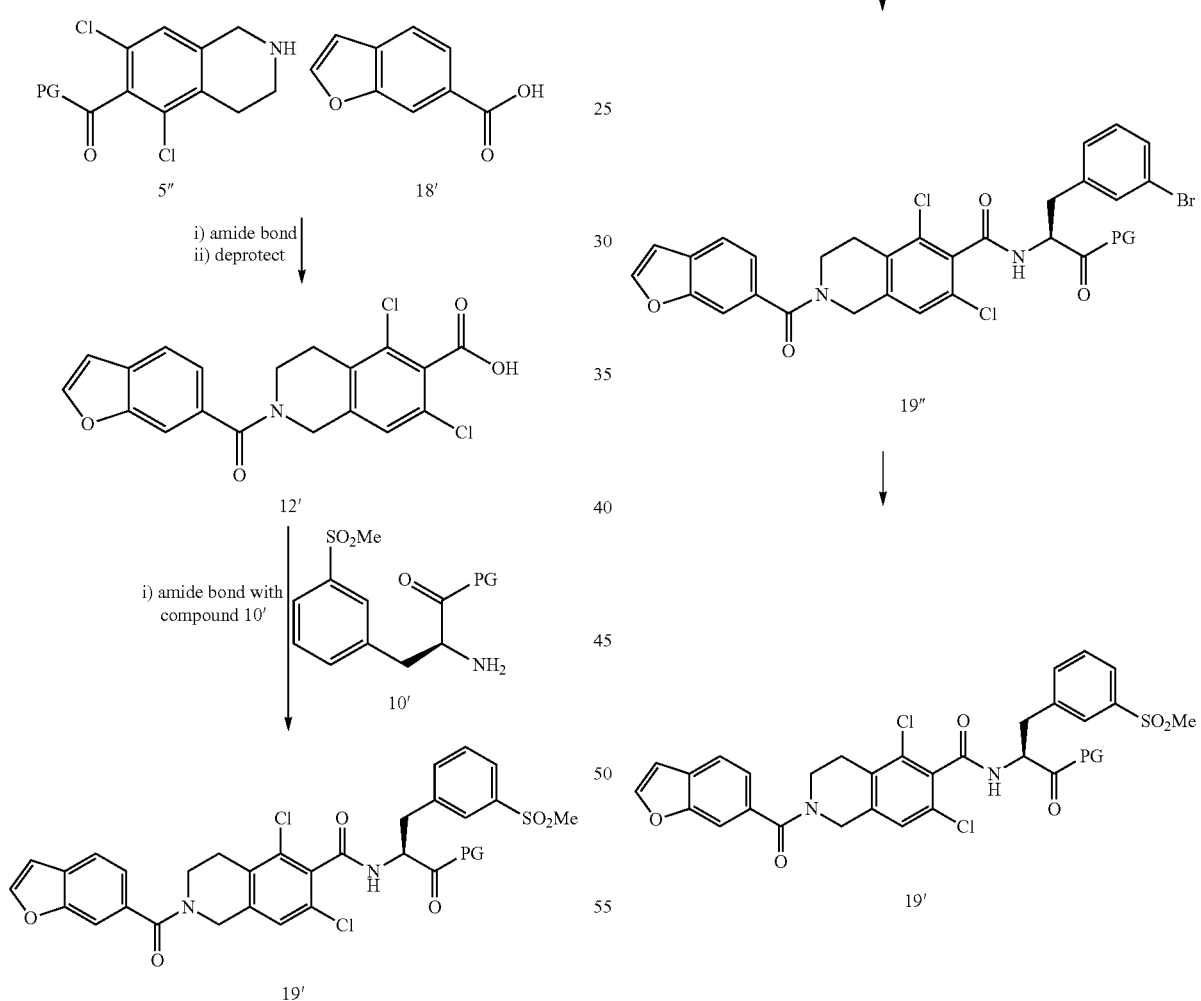

As an alternative to Schemes 3-5, compounds 18' and 5" may be coupled through amide bond formation followed by deprotection of the remaining carboxylic group to form compound 12". Amide bond formation between compound 12" and 10' yields compound 19' with a protected carboxylic group.

As an alternative to Schemes 1-5, compounds 12" and 10" may be coupled through amide bond formation followed by introduction of a methyl sulfone functionality in place of the bromine in converting compound 19" to compound 19' (similar to Scheme 2). Alternatively, instead of a bromine, compound 10" includes X, where X is any halide (Cl, I, Br, F) or a leaving group such as OTs, OTf, or the like. Compound 12" can also be made using the following scheme:

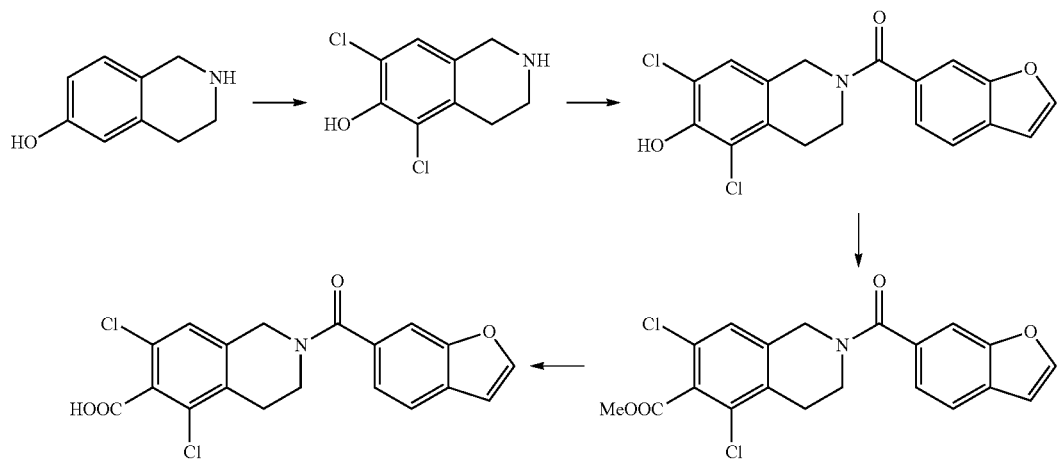

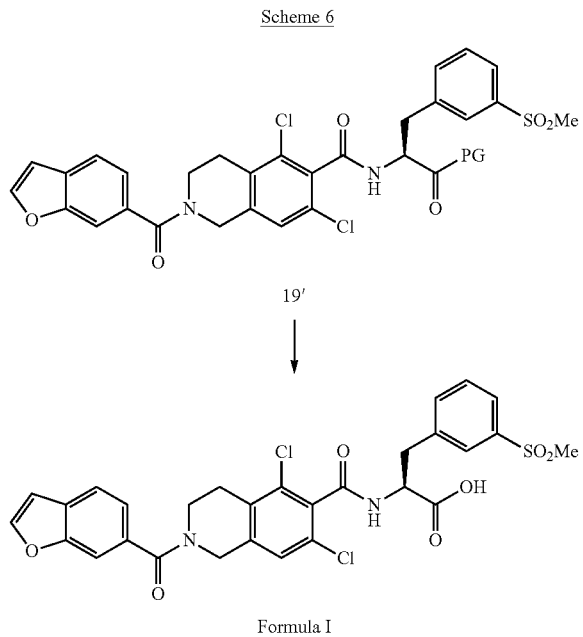

Scheme 6

Formula I

Final deprotection of compound 19' to yield the compound of Formula I or a salt thereof is accomplished in a variety of ways. In various embodiments, the resulting compound of Formula I is provided in higher optical purity and/or higher overall purity and/or higher overall yield.

In one approach, an ester protecting group is removed with acid catalyzed hydrolysis. For example, a methyl ester protecting group is removed with acid catalyzed hydrolysis. Alternatively, a benzyl ester protecting group is removed with acid, for example HCl in dioxane. The solvent for acid-catalyzed hydrolysis may be any industrially available solvent such as an aprotic solvent, a protic solvent, a polar solvent, a non-polar solvent, an ionic solvent, or a pressurized gas such as supercritical carbon dioxide. In various embodiments, the solvent is an aprotic solvent such as dioxane or tetrahydrofuran or acetone. Variously, the solvent may be selected from hexane, benzene, toluene, 1,4-dioxane, chloroform, diethyl ether, dichloromethane, tetrahydrofuran, ethyl acetate, acetone, dimethylformamide, acetonitrile, dimethyl sulfoxide, n-butanol, isopropanol, n-propanol, ethanol, methanol, water, formic acid, acetic acid, trifluoroacetic acid, and combinations thereof, such as aqueous acetone. The acid may be any acid used for hydrolysis reactions. In various embodiments, the acid is a mineral acid. In various embodiments, the acid is selected from hydrogen chloride, sulfuric acid, phosphoric acid, and sulfonic acids. In various embodiments, the acid is trifluoroacetic acid. In one embodiment, the ester may be removed by nucleophilic displacement, such as using sodium iodide in dimethylsulfoxide.

In one approach, a benzyl ester protecting group is removed with palladium on carbon. For example, the benzyl ester of compound 19' is removed by transfer hydrogenolysis using 10% palladium on carbon, using formic acid and triethylamine in a 5:1 mixture of methanol:THF, to produce the compound of Formula I.

In various embodiments, the compound 19' is a compound of Formula AA. A general strategy to convert a compound of Formula AA is provided by base hydrolysis of the ester to yield the compound of Formula I.

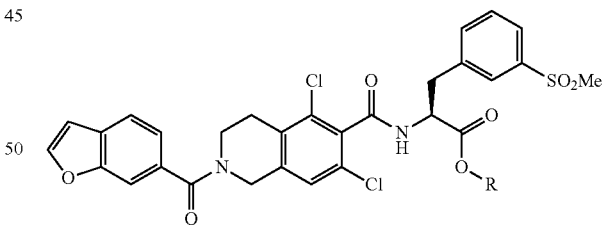

Formula AA

The compound of Formula AA may be reacted with a base in a solvent to accomplish the base-catalyzed saponification of Formula AA to yield the compound of Formula I.

The saponification solvent may be any industrially available solvent such as an aprotic solvent, a protic solvent, a polar solvent, a non-polar solvent, an ionic solvent, or a pressurized gas such as supercritical carbon dioxide. In various embodiments, the solvent is an aprotic solvent such as dioxane or tetrahydrofuran or acetone. Variously, the solvent may be selected from hexane, benzene, toluene, 1,4-dioxane, chloroform, diethyl ether, dichloromethane, tetrahydrofuran, ethyl acetate, acetone, dimethylformamide, acetonitrile, dimethyl sulfoxide, n-butanol, isopropanol, n-propanol, ethanol, methanol, water, and combinations thereof. In a preferred embodiment, the solvent is aqueous acetone. The base may be any base used for saponification reactions. In various embodiments, the base is a hydroxide such as potassium hydroxide or sodium hydroxide or lithium hydroxide.

In various embodiments, the R group is any carbon containing moiety. Such compounds may be useful as synthetic intermediates of compounds of Formula I, or as prodrugs of Formula I. Within the group where R is any carbon containing moiety, R may be selected from lower alkyl, lower alkenyl, lower alkynyl, cyclo(lower)alkyl, cyclo(lower)alkenyl, aryl, aralkyl, heterocyclyl, and heteroaryl, any of which can be substituted or unsubstituted. In various embodiments, the lower alkyl group is methyl, ethyl, propyl, isopropyl, butyl, pentyl, isobutyl, t-butyl, or hexyl. In various embodiments, the R group of Formula AA is a benzyl group. In various embodiments of Formula AA, the carbon-containing moiety R does not include a benzyl group.

In various embodiments the R group is a silyl-containing moiety such that Formula AA is a silyl ester.

In one embodiment, an ester protecting group is removed with base catalyzed hydrolysis in a homogeneous reaction such as a reaction in solution. For example, a benzyl ester protecting group is removed with NaOH in aqueous dioxane. In one embodiment, a benzyl ester protecting group is removed with NaOH in aqueous acetone. In various embodiments of a homogeneous liquid reaction, NaOH may range from about 0.1N to about 2N, such as about 0.5 N, 0.6 N, 0.7 N, 0.8 N, 0.9 N, 1.0 N, 1.1 N, 1.2 N, 1.3 N, 1.4 N, or 1.5 N, with all listed concentrations understood to be "about".

In one embodiment, an ester protecting group is removed from Compound 19' or Formula AA with base catalyzed hydrolysis in a heterogeneous reaction in the presence of phase transfer catalyst. For example, Compound 19' or a compound of Formula AA is contacted with phase transfer catalyst in aqueous acetone. In various embodiments, the reaction occurs in the presence of a solid-liquid interface. In various embodiments, the reaction occurs in a slurry of solvent and crystalline material. In various embodiments, the reaction is biphasic. In various embodiments, the reaction begins as a biphasic batch reaction and becomes increasingly homogeneous as the reaction proceeds and starting material is converted to product which remains in solution. In various embodiments, racemization of starting material is minimized by reducing exposure of unreacted starting material to base through the use of biphasic conditions.

In various embodiments, the progress of the reaction is monitored by assessing the level of solid material remaining. In various embodiments, the reaction is deemed to be essentially complete when the reaction mixture is essentially monophasic (i.e. all solids have been dissolved into solution).

In various embodiments, base hydrolysis is performed with an amount of base ranging from about 0.9 equivalents to about 3 equivalents, such as about 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 equivalents, all amounts being about. In various embodiments, the amount of base ranges from about 1.0 to about 1.5 equivalents, such as about 1.2 equivalents. In various embodiments, the base is NaOH. In various embodiments, base hydrolysis is performed with NaOH as base in the presence of less than a stoichiometric amount of tetrabutylammonium hydroxide.

In various embodiments, the reaction is a batch reaction with a time to completion of greater than 0 hours and less than about 24 hours, less than about 12 hours, less than about 8 hours, less than about 6 hours, or less than about 4 hours.

In various embodiments, base catalyzed hydrolysis of compound 19' or the compound of Formula AA is performed in the presence of a phase transfer catalyst. In various embodiments, the phase transfer catalyst is a quaternary ammonium salt, a phosphonium salt, or a crown ether. In various embodiments, the phase transfer catalyst is selected from benzyltrimethylammonium chloride, hexadecyltributylphosphonium bromide, tetrabutylammonium hydroxide, tetrabutylammonium bromide, methyltrioctylammonium chloride, and tetrabutylammonium chloride. In various embodiments, the phase transfer catalyst is tetrabutylammonium hydroxide. In one embodiment, the amount of phase transfer catalyst is less than a stoichiometric amount. For example, the amount of phase transfer catalyst is about 0.01, 0.02, 0.03, 0.04, 0.05, 0.06, 0.07, 0.08, 0.09, 0.1, 0.2, 0.3, 0.4, 0.5, 0.6, 0.7, 0.8, or 0.9 equivalents, all amounts being about.

In further embodiments, the ester protecting group can be removed by other procedures known in the literature including slightly acidic and slightly basic conditions. The ester protecting groups can also be removed by treatment with ester hydrolyzing enzymes like pig liver esterase, cholesterol esterase, amino esterase, etc. The removal of the ester protecting group from Formula AA can further be achieved by application of strong acid resins, weak acid resins, strong base resins, or weak base resins.

Upon formation of the compound of Formula I as a crude compound, a variety of isolation and/or purification methods are available. The compound of Formula I may be isolated as a crude product through distillation or evaporation of solvent from the final deprotection step. Removal of solvent may be through removal to dryness, or through removal of a portion of solvent to yield a solid/liquid mixture which is filtered and/or washed. Crude compound may be purified by slurrying in a solvent such as methyl ethylketone (MEK), acetonitrile, methylene chloride, or acetone, which solvents may be aqueous or nonaqueous. The compound for Formula I may be isolated/purified through recrystallization and/or washing with additional solvents. Procedures for recrystallization in small and large scales are known in the art.

A partial list of useful solvents for the preparation and purification of the compound of Formula I includes, for example, water, aliphatic solvents such as pentane, petroleum ether, and hexane; aromatic solvents such as toluene and xylene, aliphatic ketones and esters such as methyl ethyl ketone, acetone, ethyl acetate, isopropyl acetate, and butyl acetate, alcohols, such as ethyl alcohol, propyl alcohol, and methyl alcohol, acetonitrile, ethers, such as ethyl ether, tert-butyl methyl ether (TBME), and tetrahydrofuran, alkenes and alkynes, alkenyl esters and alcohols, alkynyl esters and alcohols, and aromatic esters and alcohols. In one embodiment, recrystallization is performed in pharmaceutically acceptable solvent(s). In one embodiment, a useful solvent is aqueous acetone.

In various embodiments, recrystallization is performed with from about 0.5 volumes to about 15 volumes of recrystallization solvent, for example from about 5 volumes to about 15 volumes, or for example about 1, 2, 3, 4, 5, 6, 7, 8, or 9 volumes. In various embodiments, recrystallization is performed with at least about 10 volumes of recrystallization solvent. In various embodiments, recrystallization provides one or more crops of crystals, for example 1 crop, 2 crops, 3 crops, or more. In various embodiments, recrystallization provides a yield of at least 50%, or at least 60%, or at least 70%, or at least 80%, or at least 90% in a first filtration and/or in a combination of filtrations.

In various embodiments, final deprotection and/or recrystallization is performed in aqueous acetone. Water and acetone are miscible thus allowing for a range from 100%/0% water/acetone to 0%/100% water acetone. In various embodiments, the ratio of water/acetone is about 10/90, 20/80, 30/70, 40/60, 50/50, 60/40, 70/30, 80/20, or 90/10, all amounts being "about". Preferably, the solvent for final deprotection and/or recrystallization is about 30% aqueous acetone. In various embodiments, recrystallization with aqueous aceone provides a yield of at least 50%, or at least 60%, or at least 70%, or at least 80%, or at least 90% in the first filtration and/or in a combination of filtrations. In various embodiments, aqueous acetone is used from about 0.5 volumes to about 15 volumes, such as about 7 volumes, as provided above.

In various embodiments, a pH modifier is used during isolation and/or purification of the compound of Formula I. Without wishing to be bound by theory, it is believed that the solubility of the compound of Formula I is modified by exposing a salt of the compound of Formula I to acidic conditions such that the carboxylic acid moiety of the compound of Formula I is protonated, thus making the compound of Formula I more soluble in organic solvents. In various embodiments, a pH modifier is added to a composition of crude compound of Formula I to produce a pH less than about 7. In various embodiments, the pH is lowered to less than about 5, less than about 4, or less than about 3. In various embodiments, the pH is within a range of about 1 to about 5. In various embodiments, the pH is about 2. The pH modifier may be an acid, such as an organic or mineral acid. In various embodiments, the pH modifier is hydrochloric acid. In various embodiments, the pH modifier is dilute HCl solution, such as 4 N HCl, 1 N HCl solution, 0.1 N HCl, or 0.01 N HCl solution. In various embodiments, local pH of less than about 1 is avoided so as to reduce racemization and/or hydrolysis.

In various embodiments, recrystallization is performed at a temperature above room temperature. In various embodiments, recrystallization is performed at a temperature between about 50 C and about 90 C. In various embodiments, compound of Formula I is dissolved in recrystallization solvent at a temperature above room temperature, filtered to remove particulates, cooled to room temperature or less than room temperature such that crystallization occurs, and filtered to separate crystals and mother liquor.

In various embodiments, recrystallization is performed in a batch process with a time to completion of greater than 0 hours and less than about 3 days, less than about 2 days, less than about 36 hours, less than about 24 hours, less than about 12 hours, less than about 8 hours, less than about 6 hours, or less than about 4 hours.

In various embodiments, recrystallization is performed in a batch process on a scale larger than about 10 kilograms, 100 kilograms, one metric ton, or 10 metric tons, all amounts being about. In various embodiments, final deprotection and/or recrystallization is performed with a yield of at least 60%, or at least 70%, or at least 80%, or at least 90% in the first filtration and/or in a combination of filtrations.

In further embodiments, the compound Formula I can be purified by other procedures known in the literature including but not limited to crashing out of a solution, freeze-drying or lyophilization, dialysis, or the like.

In some of the embodiments of the methods of manufacture of the invention, the chiral purity of the compound of Formula I as measured by chiral chromatography at 260 nm is greater than about 75%, about 75.5%, about 76%, about 76.5%, about 77%, about 77.5%, about 78%, about 78.5%, about 79%, about 79.5%, about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% of the S-enantiomer. In various embodiments, the chiral purity of the compound of Formula I as measure by chiral chromatography is greater than about 99%. In some embodiments, the chiral purity of the compound of Formula I as measured by chiral chromatography at 260 nm is about 100%.

In some of the embodiments of the methods of manufacture of the invention, the compound of Formula I has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained or produced as a result of the chemical synthesis, as measured by chromatography at 220 nm. In some embodiments, the impurity is a by-product of the synthesis. In various embodiments, the impurity is a bromine-containing compound. In various embodiments, the impurity is a mono-chloro compound.

In some of the embodiments of the method of manufacture of the invention, the compound of Formula I comprises less than about 3.0%, about 2.8%, about 2.6%, about 2.4%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, or about 0.09% of total impurities introduced, obtained or produced as a results of the chemical synthesis, as measured by chromatography at 220 nm. In some embodiments the impurities comprise a by-product of the chemical synthesis.

In one embodiment, the product of recrystallization has less than 0.5%, 0.4%, 0.3%, 0.2%, or 0.1% non-pharmaceutically acceptable solvent. In various embodiments, the product of recrystallization is essentially free of non-pharmaceutically acceptable sovlents. In one embodiment, the product of recrystallization has less than 0.5%, 0.4%, 0.3%, 0.2%, or 0.1% methyl ethyl ketone.

In various embodiments, compounds synthesized according to the invention may have various advantages, such as ease of purification, reduced cost, reduced number of synthetic steps, higher overall yields, reduced impurities, differing impurity profiles, and reduced racemization of the chiral center. In one embodiment, the compound synthesized according to the invention has an enantiomeric excess (ee) selected from greater than about 95% ee, about 96%, about 97%, about 98%, about 99%, and about 99.9%. In various embodiments, the compound synthesized according to the invention has reduced levels of chemical catalyst as an impurity compared to a compound of Formula I made using palladium as a catalyst to remove an ester group to yield the carboxylic acid. For example, in various embodiments, the compound has less than 100 ppm contamination with palladium, or less than 50 ppm, or less than 10 ppm, or less than 1 ppm contamination with palladium. In various embodiments, the compound is essentially free of chemical catalyst.

The anhydrous form of Formula I and five polymorphs, Forms A, B, C, D and E, have been previously isolated and characterized. See U.S. Pat. No. 8,080,562. Herein, a novel polymorph of Formula I has been identified, isolated and fully characterized. These six Forms are now referred as Forms I-VI, as shown in Table 1, which summarizes the relationship between the previously assigned and current nomenclature.

TABLE 1

| Form | Previous assignment |
|---|---|
| I (Channel Hydrate) | A |
| II (Monohydrate) | — |
| III (Monohydrate) | E |
| IV (Monohydrate) | C |
| V (Anhydrate) | B |
| VI (Hydrate) | D |

Pharmaceutical Compositions and Formulations and Kits

In various embodiments, the amorphous form or any of the crystalline Forms A, B, C, D, or E, or a combination thereof of the compound of Formula I are administered in pharmaceutical compositions. The pharmaceutical compositions of the invention comprise pharmaceutically acceptable carriers and excipients as well as the amorphous form or any of the crystalline Forms A, B, C, D, or E, or a combination thereof of the compound of Formula I, in order to formulate the composition for appropriate administration to the subject.

In some of the embodiments of the invention, the crystalline form remains in crystalline form in the pharmaceutical composition. In other embodiments, the amorphous form and/or crystalline form is solubilized and is no longer crystalline. In the latter case, however, the superior purity or other physicochemical properties of the amorphous form and/or crystalline form contributes to, i.e., for example, ease of handling the form of the compound of Formula I to form the composition, superior storage capabilities of crystalline form prior to formulation, better therapeutic index, tolerability of the compound of Formula I to the subject, or decreased side effects of the compound of Formula I. The amorphous form or crystalline Forms A, B, C, D, or E may be milled to provide desirable properties for formulation.

The pharmaceutical compositions of the invention may be formulated as a gel, cream, lotion, solution, suspension, emulsion, ointment, powder, crystalline forms, spray, aerosol, foam, salve, paste, plaster, paint, microparticle, nanoparticle, or bioadhesive, and may be prepared so as to contain liposomes, micelles and/or microspheres. Oral formulations can be tablets, capsules, troches, pills, wafers, chewing gums, lozenges, aqueous solutions or suspensions, oily suspensions, syrups, elixirs, or dispersible powders or granules, and the like and may be made in any way known in the art. Oral formulations may also contain sweetening, flavoring, coloring and preservative agents.

The amorphous form or any of the crystalline forms of the compound of Formula I, or a combination thereof, may be formulated as a sterile solution or suspension, in suitable vehicles, well known in the art. Suitable formulations and additional carriers and excipients are described in Remington "The Science and Practice of Pharmacy" (20$^{th}$ Ed., Lippincott Williams & Wilkins, Baltimore Md.), the teachings of which are incorporated by reference in their entirety herein.

The formulations of the invention can further include other pharmacological active ingredients as far as they do not contradict the purpose of the present invention. In a combination of plural active ingredients, their respective contents may be suitably increased or decreased in consideration of their effects and safety.

The invention also provides kits. The kits include a compound of the invention in suitable packaging, and written material that can include instructions for use, discussion of clinical studies, listing of side effects, and the like. The kit may further contain another therapeutic agent that is co-administered with the compound of Formula I, including the amorphous form or any of the crystalline Forms of the compound of Formula I or a combination thereof. In some embodiments, the therapeutic agent and the amorphous form or any of the crystalline Forms of the compound of Formula I or a combination thereof are provided as separate compositions in separate containers within the kit. In some embodiments, the therapeutic agent and the amorphous form or any of the crystalline forms of the compound of Formula I or a combination thereof are provided as a single composition within a container in the kit. Suitable packaging and additional articles for use (e.g., measuring cup for liquid preparations, foil wrapping to minimize exposure to air, dispensers, and the like) are known in the art and may be included in the kit.

Additional information regarding pharmaceutical compositions, formulations, and kits can be found in U.S. Pat. No. 8,080,562; US Patent Publication 2009/0298869; US Patent Publication 2011/0092707; U.S. Pat. No. 8,084,047; US 2010/0092542; and US Patent Publication 2006/0281739; the entire contents of each of which are incorporated by reference.

Methods of Use

Not intending to limit methods of use by a single mechanism of action, methods disclosed herein involve the inhibition of initiation and progression of inflammation related disease by inhibiting the interaction between LFA-1 and ICAM-1 by administering the compound of Formula I, including the amorphous form or any of the crystalline Forms A, B, C, D, or E, or a combination thereof, of the compound of Formula I. In some embodiments, such methods provide anti-inflammatory effects in-vitro and in-vivo, and are useful in the treatment of inflammation mediated diseases and/or the investigation of disease mechanisms.

Formula I

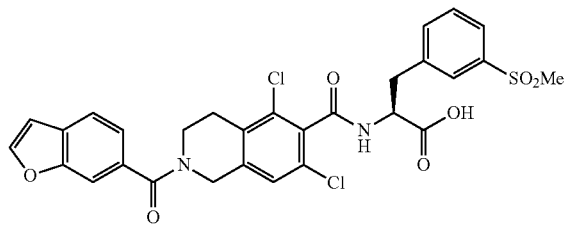

In particular, the amorphous form or any of the crystalline Forms A, B, C, D, or E, or a combination thereof, of the compound of Formula I can modulate inflammation mediated by leukocytes. The amorphous form or any of the crystalline Forms A, B, C, D, or E, or a combination thereof, of the compound of Formula I can be used as a therapeutic agent in any disorder in which antibodies to LFA-1 are shown to be effective. In one embodiment of the invention, a subject is administered the amorphous form or any of the crystalline Forms A, B, C, D, or E, or a combination thereof, of the compound of Formula I to modulate inflammation associated with ocular inflammation. Another embodiment of the methods, a subject with inflammation associated with dry eye syndrome is administered the amorphous form or any of the crystalline Forms A, B, C, D, or E, or a combination thereof, of the compound of Formula I.

Administration of a pharmaceutical composition comprising the compound of Formula I, including the amorphous form or any of crystalline Forms A, B, C, D, or E, or a combination thereof, of the compound of Formula I may be by any suitable means. In some embodiments, a pharmaceutical composition comprising the amorphous form or any of crystalline Forms A, B, C, D, or E, or a combination thereof, of the compound of Formula I, is administered by oral, transdermal, by injection, slow release intraocular implantation, or aerosol administration.

Additional information regarding uses of the compound of Formula I can be found in U.S. Pat. No. 8,080,562; US Patent Publication 2009/0298869; US Patent Publication 2011/

0092707; U.S. Pat. No. 8,084,047; US 2010/0092542; and US Patent Publication 2006/0281739; the entire contents of each of which are incorporated by reference. Additional information regarding administration of the compound of Formula I can be found in U.S. Pat. No. 8,080,562; US Patent Publication 2009/0298869; US Patent Publication 2011/0092707; U.S. Pat. No. 8,084,047; US 2010/0092542; and US Patent Publication 2006/0281739; the entire contents of each of which are incorporated by reference.

EXAMPLES

Example 1

Scheme E1

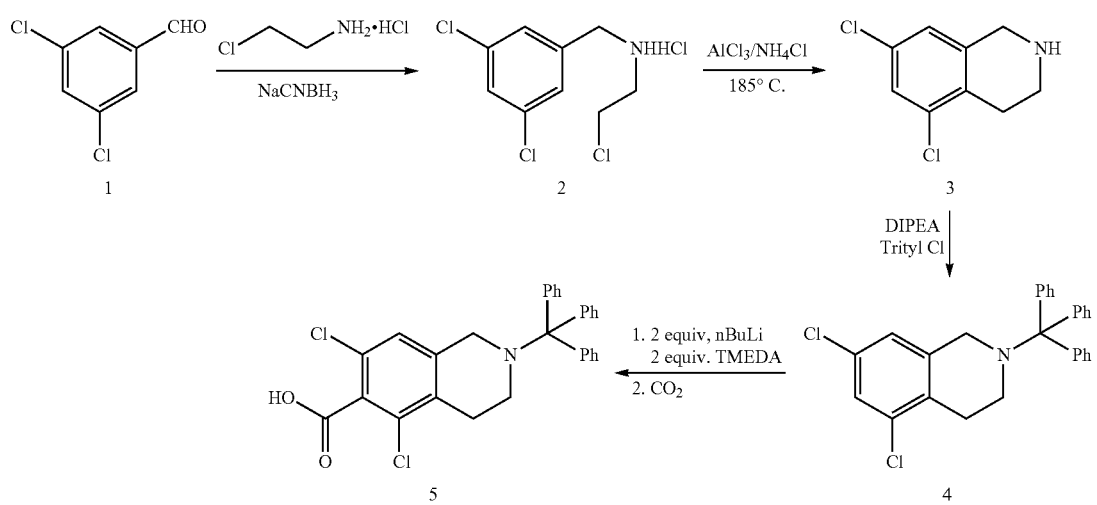

Reductively aminating 3,5-dichlorobenzaldehyde, compound 1, with 1-chloro-2-aminoethane and sodium cyanoborohydride provided 35% yield of compound 2. Cyclization of compound 2 using aluminum chloride catalysis and ammoniun chloride at 185° C. provided compound 3 in 91% yield. Protection of the free amine of compound 3 as the trityl protected species afforded compound 4 in 89% yield. A carboxylic acid functionality was introduced by treatment of compound 4 with n-butyllithium (nBuLi) and tetramethylethylenediamine (TMEDA), with subsequent introduction of carbon dioxide, to produce trityl protected compound 5 in 75% yield.

Example 1A

Scheme E1A

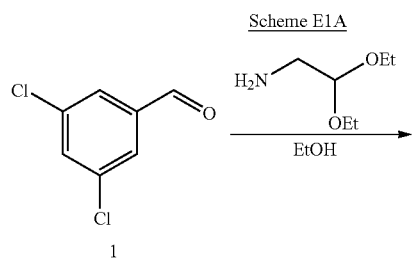

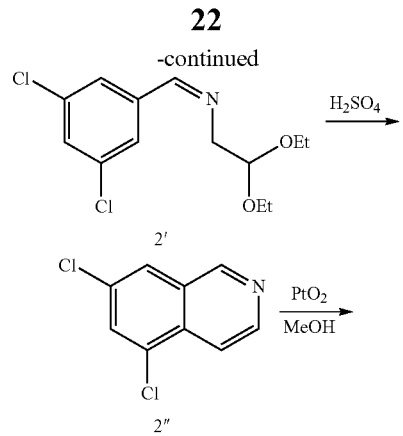

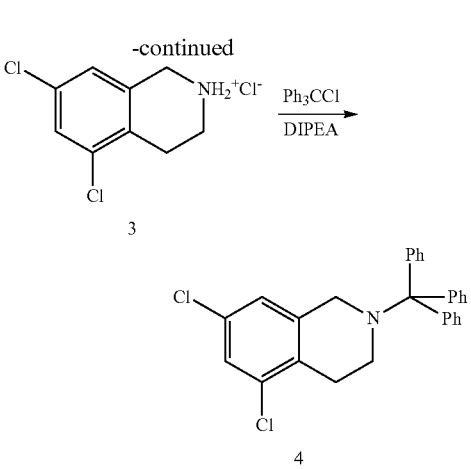

To a glass reactor was charged 3,5-dichlorobenzaldehyde. Absolute ethanol was added to the batch slowly (this addition is mildly exothermic) and agitation started. 2,2-Diethoxyethylamine (1.03 equiv) was slowly added to the batch, keeping the batch temperature at 20-78° C. The batch was then heated to 76-78° C. for 2 h. GC-MS analysis indicated reaction completion (starting material<1%). The batch was cooled to ambient temperature for work-up. The batch was concentrated in vacuo to a residue and azeotroped with heptanes (x2). The residue was cooled and held at 0-5° C. for 12 h to form a suspension. The solids were collected by filtration and the cake was washed with cold (0-5° C.) heptanes, and dried under hot nitrogen (45-50° C.) to afford Compound 2' as a white solid (94% yield).

To a glass reactor was charged concentrated 95-98% sulfuric acid (25.9 equiv). The batch was heated to 120-125° C. and a solution of Compound 2' in CH$_2$Cl$_2$ was added slowly over 1 h, keeping the batch temperature between 120-125° C. The batch was then stirred at 120-125° C. for 6 h. The batch was cooled to <50° C. To a glass reactor was charged DI water and the batch temperature was adjusted to 0-5° C. The reaction mixture was slowly transferred, keeping the batch temperature between 0-50° C. DI water was used to aid the transfer. To the batch was added Dicalite 4200. The batch was filtered through a pad of Dicalite 4200. To the filtrate was added 50% aqueous sodium hydroxide solution slowly over 3 h, keeping the batch temperature between 0-50° C. to adjust the pH to 12. The resulting suspension was stirred at 45-50° C. for 2 h and the solids were collected by filtration. The filter cake was slurried in DI water at 30-35° C. for 1 h. The batch was filtered. The cake was washed with heptanes and dried in vacuum oven at 45-50° C. for 22 h to give crude compound 2" as a tan solid (75% yield), which was further purified by recrystallization.

To a reactor was added platinum dioxide (0.012 equiv), Compound 2", and MeOH (10 vol) and the suspension was stirred at room temperature under argon for 10 minutes. The reaction mixture was inerted with argon three times and then stirred under 125 psi of hydrogen at room temperature for 25 hours. HPLC analysis indicated complete reaction with less than 1% of the starting material remaining After standing, the supernatant was decanted from the solids (catalyst) by vacuum. To the solids was added methanol and the slurry was mixed under nitrogen. The solids were allowed to settle on the bottom over several hours. The supernatant was decanted from the solids by vacuum. The combined supernatants were filtered through Celite under a blanket of nitrogen and the filter pad was washed with MeOH (x2). The combined filtrate and washes were concentrated to dryness. The residue was slurried in MTBE. The mixture was treated with 3 M HCl while maintaining the temperature <40° C. resulting in the formation of a heavy precipitate. The mixture was stirred at 35-40° C. for 60 to 90 minutes. The batch was cooled to 0-5° C., stirred for 60 to 90 minutes and then filtered. The filter cake was washed with cold DI water (x2) followed by a displacement wash with MTBE (x2). The filter cake was dried under reduced pressure to afford Compound 3 Hydrochloride Salt (86% yield). The hydrogenation catalyst can be recovered and re-used.

Compound 3 and trityl chloride were added to the reaction flask. DCM (10 vol) was added to the reactor and agitation was started to form slurry. The reaction mixture was cooled to 10-15° C. N,N-Diisopropylethylamine (2.5 equiv) was slowly added to the reaction mixture, maintaining the temperature at 15-25° C. during the addition. Once addition was complete, the batch was stirred at 15 to 25° C. for a minimum of 60 minutes. The reaction was assayed by HPLC by diluting a sample with acetonitrile and then injecting it on the HPLC. The first assay after 30 minutes indicated that the reaction was complete with <1% of starting material observed by HPLC analysis. The reaction mixture was diluted with DI water (5 vol). The reaction mixture was stirred for 5 minutes after which it was transferred into a separation funnel and the phases were allowed to separate. The DCM layer was washed with DI water (5 vol) by stirring for 5 minutes and then allowing the phases to separate. The DCM layer was washed with brine (5 vol) by stirring for 5 minutes and then allowing the phases to separate. The DCM layer was dried over magnesium sulfate, filtered and the filter cake was washed with DCM (x2). The combined filtrate and washes were concentrated to a residue that was azeotroped with EtOAc (x2). The residue was suspended in EtOAc and stirred for 1 hour in a 40° C. water bath. The resulting slurry was cooled to 0-5° C. for 1 hour and then filtered. The filter cake was washed twice with EtOAc and then dried under reduced pressure to afford Compound 4.

Example 1B

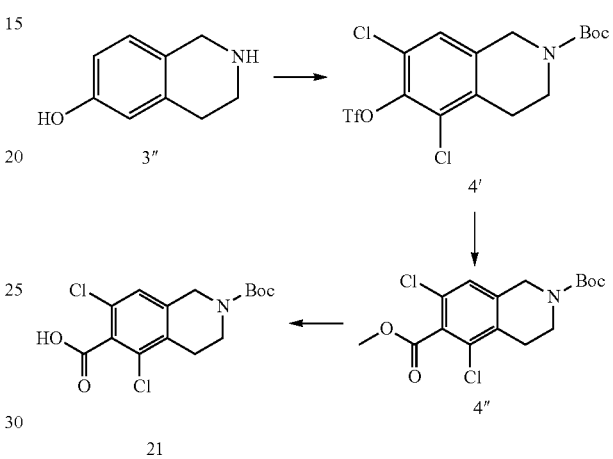

To 1,2,3,4-tetrahydro-6-hydroxy-isoqinoline in acetonitrile was added p-toluenesulfonic acid and N-chlorosuccinimide. The suspension was cooled to ambient temperature, and the product isolated by filtration for a yield of approximately 61% with purity greater than 95%. The isolated TsOH salt was recrystallized until purity was greater than 99.7%. To one equivalent of the TsOH salt suspended in methanol was added 2M sodium carbonate (0.55 eq.) and 1.2 eq. of Boc anhydride. The suspension was stirred at room temperature overnight. The reaction was monitored by HPLC. Upon completion, the mixture was cooled to below 10° C., water was added, and the Boc-protected dichloro compound was isolated by filtraton. The product was washed and dried at 40° C. for a yield of 95% and purity of >97%. The Boc-protected dichloro compound was suspended in dichloromethane (10 volumes) and pyridine (5 volumes) was added. The mixture was cooled to below 2° C., and triflic anhydride (1.25 eq) was added. The mixture was stirred at 0-2° C. for 10 minutes, and then poured into 10 volumes of 6% aqueous sodium hydrogen carbonate solution. After washing with dichloromethane, the organic phases were combined and dried over magnesium sulphate. Following purification, the product (Compound 4') was obtained in 90% yield and >98% purity. Compound 4' was dissolved in dimethylformamide and methanol at room temperature. Diisopropylamine (4 eq) was added. Under CO atmosphere, 1,3-bis(diphenylphosphino)propane (0.1 eq) and palladium acetate (0.1 eq) was added. The reaction was heated to reflux, and monitored by HPLC. Upon near completion, the mixture was cooled to ambient temperature. Workup with water, ethyl aceate, and brine yielded Compound 4", which was used without further purification. Compound 4" was dissolved in methanol and 2.4 M sodium hydroxide (10 volumes each) and refluxed. The mixture was cooled to ambient temperature, and toluene was added. Following aqueous workup, the pH was adjusted to 2.3 with 3M hydrochloric acid, and crude product was isolated by filtration in 53% yield with greater than 80% purity.

Example 2

Scheme E2

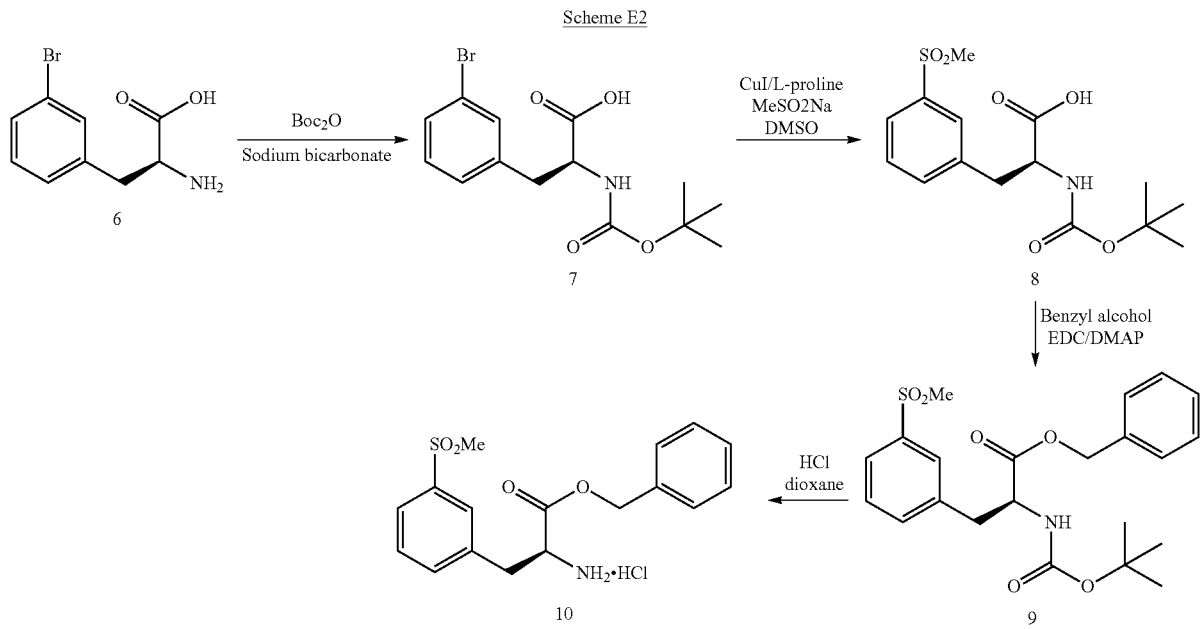

t-Butylcarbamate (Boc) protection of the amino group of bromophenylalanine was accomplished, using sodium bicarbonate (3 equivalents), t-butyl dicarbonate (Boc$_2$O, 1.1 equivalent) in dioxane and water, to obtain compound 7 in 98% yield. A methyl sulfone functionality was introduced by treating the bromo compound 7 with copper iodide (0.4 equivalents), cesium carbonate (0.5 equivalents), L-proline (0.8 equivalents), and the sodium salt of methanesulfinic acid (3.9 equivalents) in dimethylsulfoxide (DMSO) at 95-100° C. for a total of 9 hours, with two further additions of copper iodide (0.2 equivalents) and L-proline (0.4 equivalents) during that period. Compound 8 was isolated in 96% yield. The carboxylic acid of compound 8 was converted to the benzyl ester, compound 9, in 99% yield, using benzyl alcohol (1.1 equivalent), dimethylaminopyridine (DMAP, 0.1 equivalent) and N-(3-dimethylaminopropyl)-N-ethylcarbodiimide (EDC, 1.0 equivalent). The amino group of compound 9 is deprotected by adding a 4N solution of HCl in dioxane to compound 9 at 0° C. in methylene chloride. The HCl salt of the free amino species, compound 10 was isolated in 94% yield.

Example 2A

Example 2 was repeated with potassium carbonate in place of cesium carbonate.

Example 2B

Boc-protected bromophenylalanine (Compound 7) (100 g) was dissolved in DMSO (400 mL) with stirring and degassing with argon. Sodium methane sulfinate (98 g), copper iodide (28.7 g), potassium carbonate (40 g) and L-proline (26.75 g) were added at 28-30° C. Reaction was heated to about 87° C. for about 17-19 hours. Reaction was cooled and quenched with crushed ice, stirred for 30-40 minutes, and the pH was adjusted from about 12 to about 3-4 with citric acid (350 g). Quenched reaction mixture was filtered, extracted with dichloromethane x3, washed with ammonium chloride solution, washed with sodium bisulphite solution, and washed with brine. Crude product in dichloromethane was concentrated in vacuo until moisture content was below about 0.5%, and used in next step without further isolation. Crude compound 8 in dichloromethane was charged with benzyl alcohol and DMPA with stirring under nitrogen. Reaction cooled to 0-5° C. EDC-HCL (1.03 equiv) added with stirring for 30 minutes. Upon completion of reaction by TLC and HPLC, the reaction was quenched with sodium bicarbonate solution, the organic layer was separated, and the aqueous layer was extracted with dichloromethane. The organic layer was washed with citric acid solution, and combined organic layers were washed with brine solution. Dichloromethane was removed at 45-50° C., and the concentrate was used for next step without further isolation. The amino group of compound 9 was deprotected by adding a 4N solution of HCl in dioxane to compound 9 at 10-15° C. in methylene chloride. The HCl salt of the free amino species, compound 10 was isolated by filtration from diethyl ether. Isolation of compound 10 was performed through recrystallization using a dimethylformamide/dichloromethane solvent system.

Example 3

Scheme E3

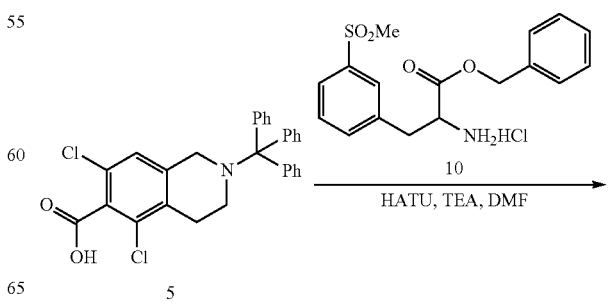

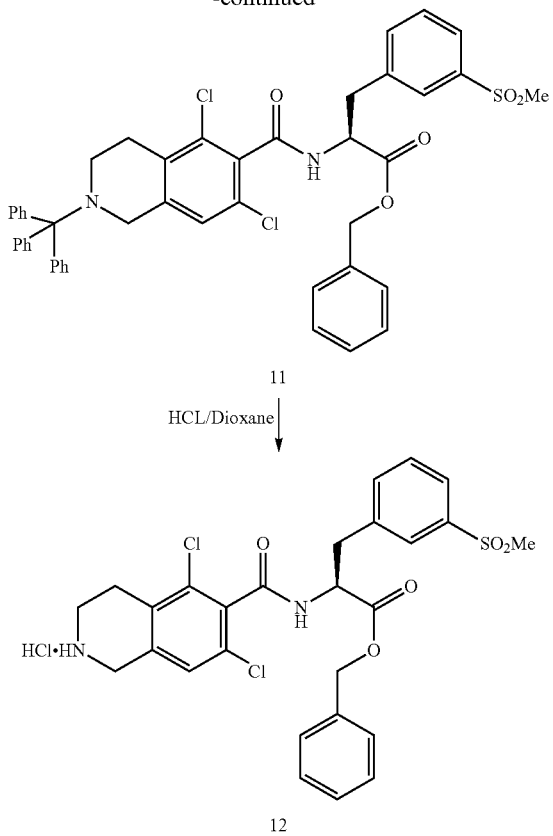

11

HCL/Dioxane ↓

12

Compound 5 was treated with triethylamine (TEA, 5 equivalents) and 2-(7-Aza-1H-benzotriazole-1-yl)-1,1,3,3-tetramethyluronium hexafluorophosphate (HATU, 1.25 equivalents) for 10 minutes in dimethylformamide (DMF), and then compound 10 was added to the solution. After stirring at room temperature for 18 hours, the product, compound 11 was isolated in 70% yield. Removal of the trityl protecting group was accomplished by treating compound 11, with HCl in dioxane (4 N, excess) at room temperature for 2 hours, diethyl ether added, and the solid product, compound 12, was isolated by filtration in 95% yield. The compound 12 exists in both amorphous and crystalline form and can be isolated in either form.

Example 3A

Compound 5 was dissolved in isopropyl acetate and cooled to 20 to 25° C. Thionyl chloride was added, with cooling to 10 to 15° C., and N-methylmorpholine was added slowly. The reaction was monitored by HPLC. Compound 10, water, and isopropyl acetate were stirred at 15 to 20° C. until a solution was achieved. N-methylmorpholine was added followed by addition of the Compound 5 reaction mixture (acid chloride of Compound 5). The reaction was monitored by HPLC. Upon completion, the biphasic layers were allowed to settle, and the aqueous layer was removed. The upper organic layer was extracted with water, and the remaining organic layer was distilled under vacuum. Dioxane and IpAc were added with further distillation. Once dry, 4N anhydrous HCl in dioxane was added. The mixture was stirred at 20 to 25° C. for 12 hours, and checked for complete deprotection by HPLC. Once complete, the thick slurry was filtered, washed with IPAc and dried under vacuum at 45 to 55° C. Yield of Compound 12 was 88%.

Example 4

The benzofuranyl carbonyl moiety of the compound of Formula I was prepared using various schemes, (Schemes E4, E4A, and E4B).

Scheme E4

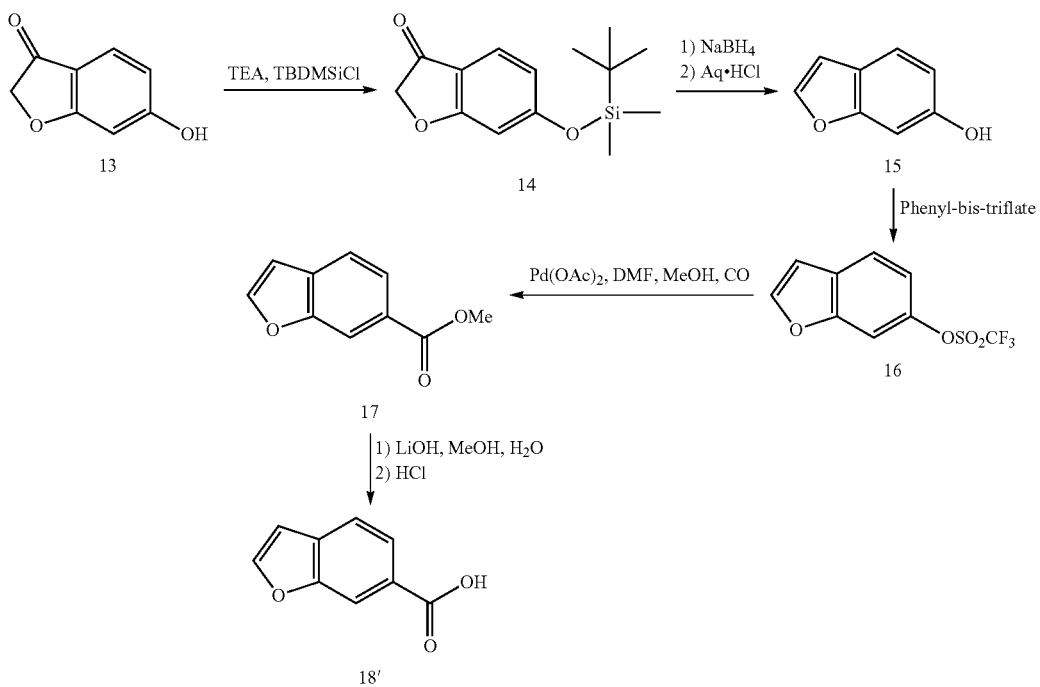

The benzofuranyl carbonyl moiety was prepared by protecting the hydroxyl group of compound 13 by reacting with tert-butyldimethylsilyl chloride (1.0 equivalents) and triethylamine (TEA, 1.1 equivalents) in acetone, to give compound 14 in 79% yield. A solution of compound 14 in methanol was then treated with sodium borohydride (1.0 equivalent) at room temperature overnight. The reaction was quenched with an addition of acetone, stirred at room temperature for a further 2.5 hours, aqueous HCl (4N) was added with the temperature controlled to below 28° C., tetrahydrofuran (THF) was added, and the solution stirred overnight under argon and in the absence of light. The product, compound 15, was isolated quantitatively by extraction into methylene chloride, concentrated at low heat, and used without further purification. The triflate ester, compound 16, was produced in 69% yield from compound 15 by reacting it with N-phenyl-bis(trifluoromethanesulfonimide) (1.0 equivalent) in methylene chloride for 72 hours. Compound 16 in a mixture of DMF, methanol, and triethylamine, was added to a prepared solution of palladium acetate, 1,3-Bis(diphenylphosphino)propane (dppp), DMF and methanol in an autoclave. Carbon monoxide was charged into the autoclave to a pressure of 8 bar, and the reaction mixture was heated at 70° C. for 6 hours. After workup, compound 17 was isolated in 91% yield. Lithium hydroxide (4 equivalents) in methanol and water was used to hydrolyze the ester and permit the isolation of compound 18' in 97% yield.

Example 4A

Example 4 was repeated with triflic anhydride and sodium hydroxide as reagents for the ester hydrolysis.

Compound 15 (6-Hydroxybenzofuran) was stirred in dichloromethane and diisopropylethylamine. Triflic anhydride (1.2 eq.) was added, keeping the temperature below 20 C. The reaction was monitored by HPLC. The reaction was quenched with methanol, solvent was removed with vacuum, and the crude residue of Compound 16 was used without further purification. Compound 16 as crude residue was dissolved in 4 volumes of dimethylformamide and 2 volumes methanol. To the solution was added 0.02 eq. of palladium acetate, 0.02 eq. of dppp, and CO under pressure. The reaction was monitored by HPLC. Following workup, Compound 17 was isolated as a crude oily residue without further purification. The residue of compound 17 was dissolved in methanol (5 volumes) and 1 volume of sodium hydroxide (27.65%) was added. The mixture was heated to 40 C until full conversion of HPLC. The mixture was cooled to ambient temperature and 3 volumes of water were added. The pH was adjusted to about 2 with 3M hydrochloric acid. The suspension was filtered, washed with water, and dried to give Compound 18' in about 75% overall yield with purity >99.5%.

Example 4B

Scheme E4B

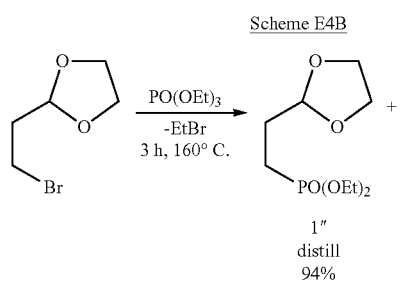

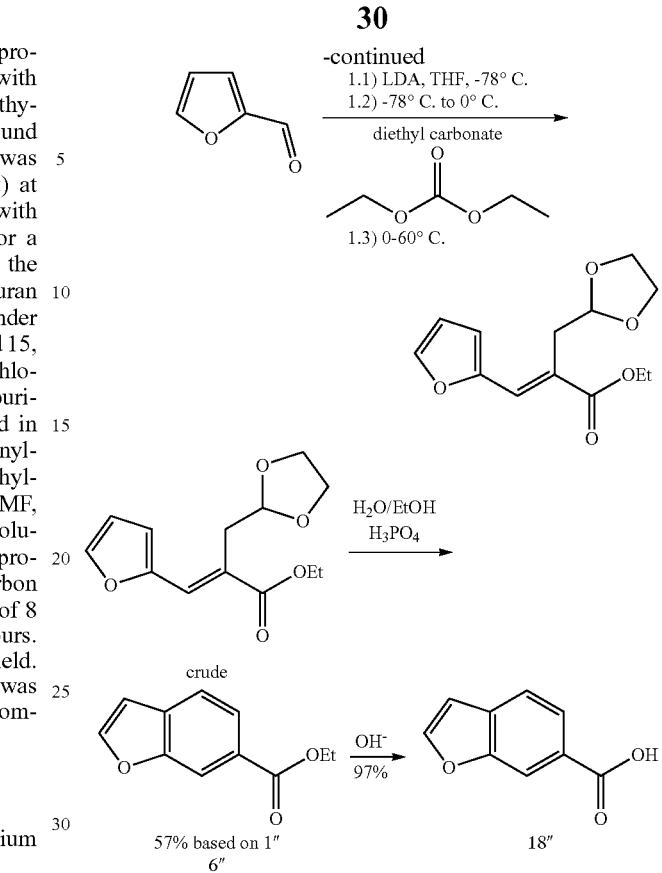

Diethyl 2-(1,3-dioxolan-2-yl)ethylphosphonate, compound 1", was prepared from 2-(2-bromoethyl)-1,3-dioxolane by the addition of triethyl phosphate. After removal of ethyl bromide through distillation at 210° C. the crude reaction mixture was cooled and then by way of vacuum distillation, compound 1" was collected as a colorless oil in 94% yield.

In the next step, n-butyllithium (2.15 equivalents) in hexane was cooled to −70° C. and diisopropylamine (2.25 equivalents) was added while keeping the temperature below −60° C. Compound 1" (1 equivalent) dissolved in tetrahydrofuran (THF) was added over 30 min at −70° C. After 10 min, diethyl carbonate (1.05 equivalents) dissolved in THF was added over 30 min keeping the reaction temperature below −60° C. After stirring for one hour at −60° C., the reaction was allowed to warm to 15° C. and furan-2-carbaldehyde (1.3 equivalents) dissolved in THF was added. After stirring for 20 hrs at room temperature, the reaction was rotary evaporated to dryness to yield ethyl 2-(((1,3-dioxolan2-yl)methyl-3-(furan-2-yl)acrylate, which was used directly in the next reaction.

The crude compound (1 equivalent) was dissolved in ethanol and added to a mixture of water and phosphoric acid (85%, 15 equivalents) over 30 min while keeping the temperature below 50° C. After stirring for 20 hrs at room temperature, another 200 ml of phosphoric acid (85%) was added and the mixture was heated to 50° C. for an additional two hrs. After removal of ethanol by rotary evaporation, the material was extacted with toluene, washed with water, dried with sodium sulfate, treated with charcoal, filtered and dried down to an oil. This oil was distilled to afford ethyl benzofuran-6-carboxylate, compound 6", (bp 111-114.5° C.) which crystallized on standing. Compound 6" was recovered at 57% yield based on compound 1".

Compound 6" (875 mmol) was dissolved in methanol and tetrahydrofuran (THF). Sodium hydroxide (4 M, 3 equivalents) was added and the reaction was stirred overnight. After concentration via rotary evaporation, the aqueous solution was extracted with methyl tert-butyl ether (MTBE), acidified to pH 2 with the addition of hydrochloric acid (HCl) and cooled resulting in fine crystals of benzofuran-6-carboxylic acid, i.e., compound 18'. Compound 18' was isolated, washed with water and dried to a final yield of 97% yield.

Example 5

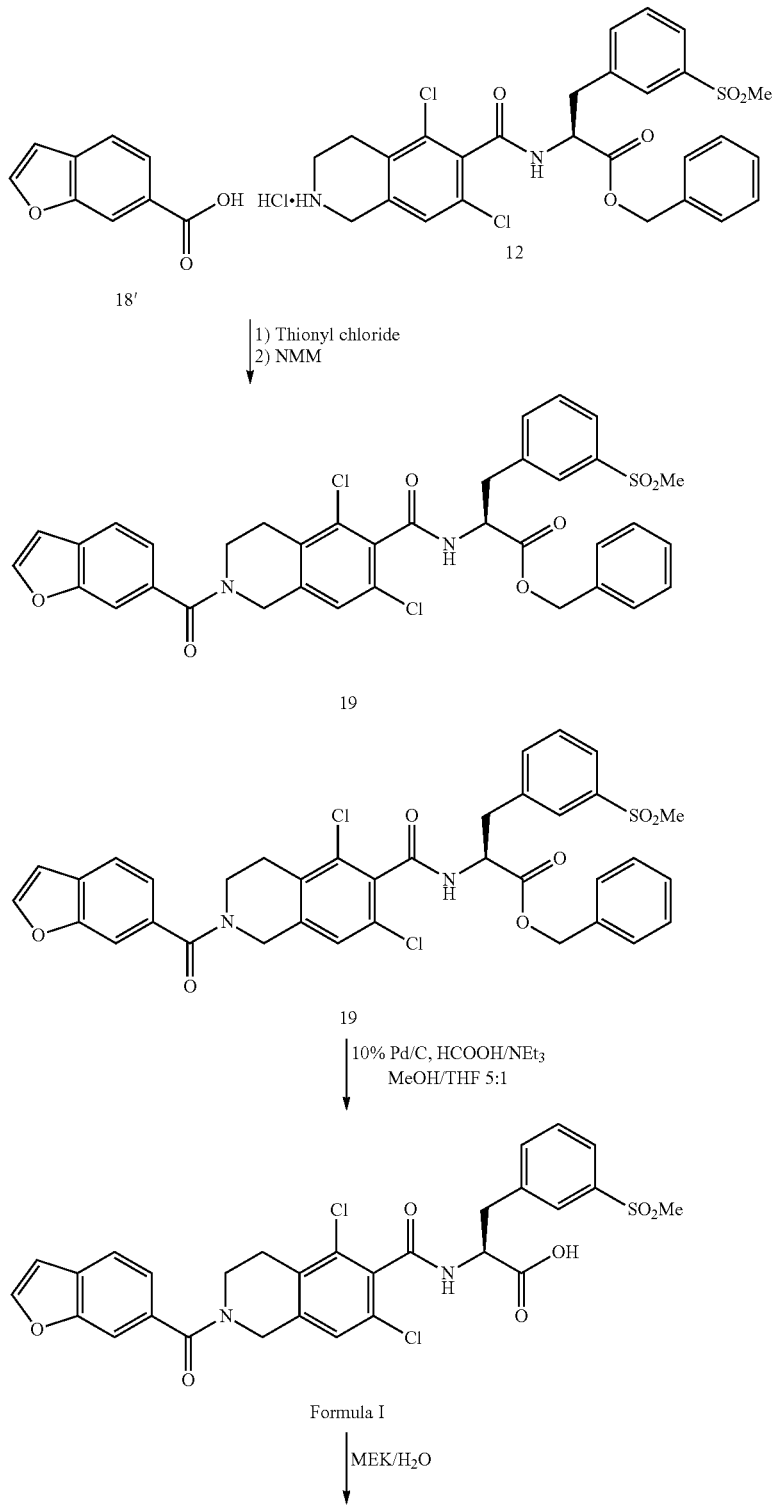

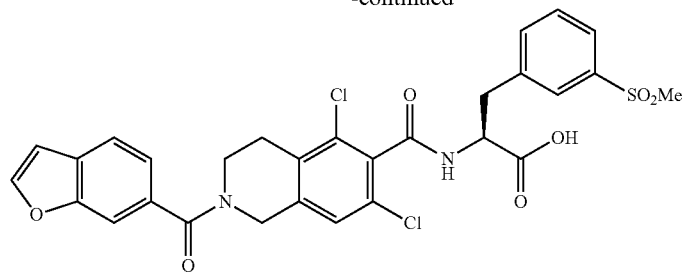

Form A of Formula I

The benzofuran carboxylic acid 18' was treated with oxalyl chloride (1.2 equivalents) and a catalytic amount of DMF, stirring for 5.5 hours until a clear solution was obtained. The solvent was removed under reduced pressure and the acid chloride of compound 18' was stored under argon until use, on the next day. The acid chloride, in methylene chloride was added slowly to a methylene chloride solution of the compound of Formula 12 and diisopropylethylamine (DIPEA) which was cooled to 0-5° C. The reaction was not permitted to rise above 5° C., and after completion of addition, was stirred at 5° C. for a further 0.5 hour. Upon aqueous workup and extraction with methylene chloride, the product, compound 19, was isolated in quantitative yield.

A final step of slurrying in methyl ethylketone (MEK) produced Form A of the compound of Formula I. The product was washed with water to remove residual MEK. Alternatively, the product of the hydrogenolysis step was slurried in acetonitrile to yield Form A of the compound of Formula I.

Taking the compound of Formula I directly as the crude reaction product after transfer hydrogenolysis, and reconcentrating down from a solution in methylene chloride, the amorphous form of the compound of Formula I was obtained in 97% purity.

Example 6

An alternative protection strategy was performed in Scheme E6.

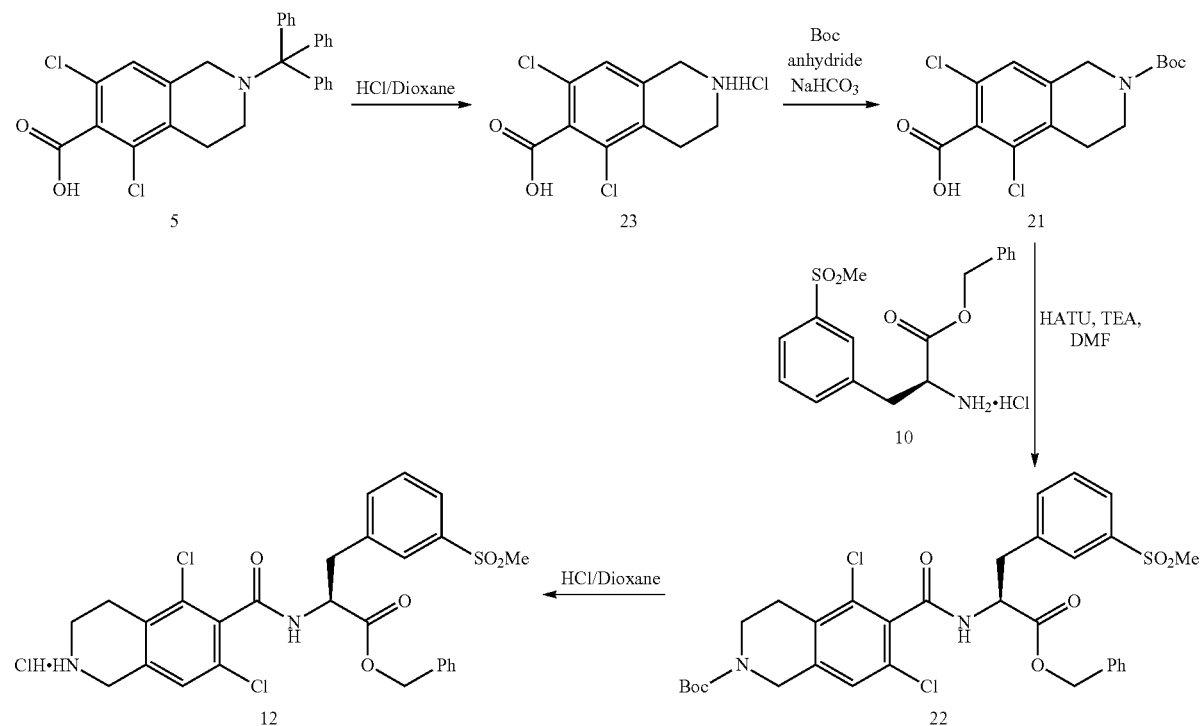

The benzyl ester of compound 19 was removed by transfer hydrogenolysis using 10% palladium on carbon, using formic acid and triethylamine in a 5:1 mixture of methanol:THF, to produce the compound of Formula I in 95% yield.

Boc-protection was used for the ring nitrogen in the intermediates 21 and 22. Compound 5 was deprotected with HCl in dioxane to produce compound 23 in better than 97% yield. Boc-protection was introduced, using di-tert-butyl dicarbonate (1.1 equivalent), and compound 21 was obtained in better than 95% yield. Compound 10 was coupled with compound 21 to obtain compound 22, using HATU and triethylamine in DMF. The product, compound 22, was obtained in quantitative yield, and greater than 90% purity. Deprotection with HCl yielded the compound of Formula 12 in 97.4% yield.

Transfer hydrogenolysis of compound 19 produced the compound of Formula I with optical purity of 98.5% (S) enantiomer compared to 79-94.5% (S) enantiomer optical purity obtained by hydrolysis of the corresponding methyl ester.

Example 6A

Example 6 was repeated with thionyl chloride to form the acid chloride for amide bond coupling in place of HATU.

Example 7

An alternate strategy to convert compound 19 into Formula I was performed by base hydrolysis of the benzyl ester (compound 19).

Scheme E7

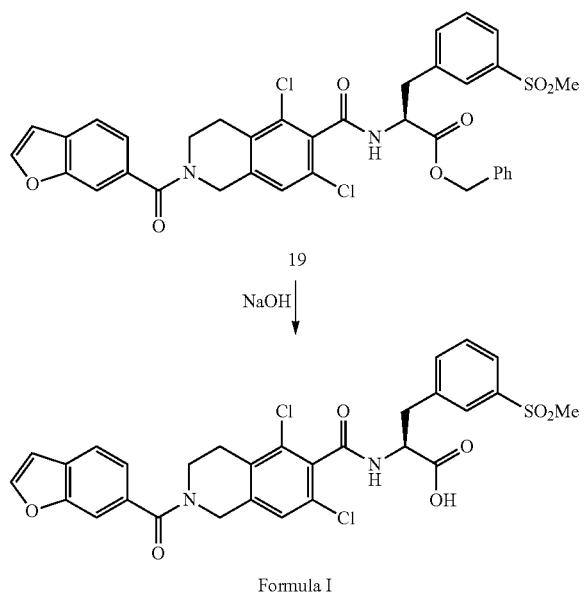

Formula I

Compound 19 ((S)-benzyl 2-(2-(benzofuran-6carbonyl)-5,7-dichloro-1,2,3,4-tetrahydroisoquinoline-6-carboxamido)-3-(3-methylsulfonyl)phenyl)propanoate) (70.9 mmol) was dissolved in dioxane and water was added. This solution was cooled to 8° C. Over 45 minutes, NaOH (0.5 M) was added to 68.0 mmol. After stirring for 2 hrs, the dioxane was removed by rotary evaporation. The aqueous solution was extracted twice with toluene to remove unreacted starting material. Ethyl actetate was added to the aqueous layer and with vigorous stirring the aqueous layer was acidified to pH 2 with HCl (4 M aqueous). After stirring, the layers were separated and the aqueous layer was extracted with ethyl acetate. The combined ethyl acetate fractions were washed with brine, dried with sodium sulfate and evaporated to dryness resulting in a foam which was 95% pure by HPLC and had a 94.8% ee. This foam was dissolved in methyl ethylketone (MEK) and was seeded with crystals (99% pure, 99% ee) which resulted in thick crystallization. After stirring for 24 hr, the suspension was filtered and washed with water and dried under vacuum. The yield of Formula I was 77% with a purity of 98.9% and 97.9% ee optical purity. An additional crop of Formula I (>98% pure) was obtained through concentration of the mother liquor.

Example 8

An alternative coupling, deprotection, and purification process was performed.

Compound 18' was dissolved in isopropyl acetate and the temperature adjusted to 20 to 25° C. Thionyl chloride was added, and the temperature was adjusted to 10 to 15° C. N-methylmorpholine was added. The reaction was monitored by HPLC. Compound 12 was dissolved in water, methyl ethyl ketone, and N-methylmorpholine, and this mixture was cooled to 15 to 20° C. The acid chloride solution of Compound 18' was added slowly and stirred for 30 minutes. The reaction was monitored by HPLC. Seeds of Compound 19 were added, and the mixture was stirred for 1 hour, and then a portion of the organic solvents were distilled under vacuum. The mixture was cooled to 20 to 25° C. and stirred for 2 hours, and filtered. The filter cake was washed with isopropyl acetate, and then the filter cake was slurried in water, filtered, washed with water, and dried at 40° C. under vacuum for a yield of 90%.

Compound 19 was mixed with acetone, water, and tetrabutylammonium hydroxide (TBAH) and stirred at 18 to 22° C. until a solution was achieved. 2N sodium hydroxide was added slowly over 1 hour, and stirred at 25° C. until HPLC indicated that the reaction was complete. The mixture was distilled under vacuum at 30 to 35° C. to remove acetone. The resulting solution was cooled to 10° C. and 4N aq HCl was added maintaining a temperature of less than 15° C., to pH ~2. The suspension that forms was stirred for about an hour, filtered, and the filter cake was washed with water. The wet cake was suspended in acetone and water (about 2/1) and warmed to 40 to 45° C. to effect solution. The solution was filtered through a 10 micron filter. The mixture was cooled to 18 to 22° C. Seeds were added and the mixture was stirred for 12 hours. The product was collected by filtration, and washed with 30% aqueous acetone, and dried under vacuum at 45 to 55° C. for a yield of 88%.

Example 9

Crude compound of Formula I was recrystallized in 10 volumes of methyl ethyl ketone with stirring for 3 days to yield purified compound of Formula I in 60-65% yield.

Example 10

Crude compound of Formula I was recrystallized in 30% aqueous acetone followed by one volume water over 24-36 hours to yield purified compound of Formula I in 73-77% yield.

Example 10A

Crude compound of Formula I is recrystallized in 30% aqueous acetone followed by one volume water over 24-36 hours to yield purified compound of Formula I in 80-90% yield with multiple filtrations. The obtained compound of Formula I has no detectable residue of methyl ethyl ketone.

Example 11

Crystalline Form II
Small Scale Synthesis
Approximately 50 mg of crystalline Form I was dissolved in acetone (2.5 mL) at 50° C. The solution was polish filtered into a preheated container. Anti-solvent, n-heptane was added and the mixture was placed in a refrigerator at about 5° C. The resulting solid was filtered and dried under vacuum.

Scale up Synthesis

Approximately 320 mg of Form I was dissolved in acetone (15 mL). The solution was polish filtered into a preheated vial. Then n-heptane (10 mL) was added and the mixture was refrigerated for 30 min. The cooled solution was seeded with Form II material and allowed to equilibrate for 12 h at 5° C. The resulting solid was filtered and dried overnight under vacuum.

Figure 4:
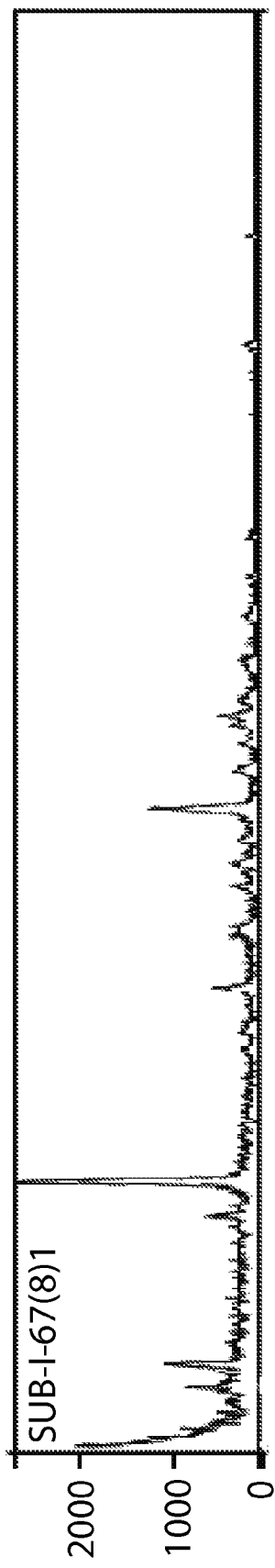
FIG. 4 is a graphical representation of the X-ray powder diffraction pattern of crystalline Form II.
Figure 5:
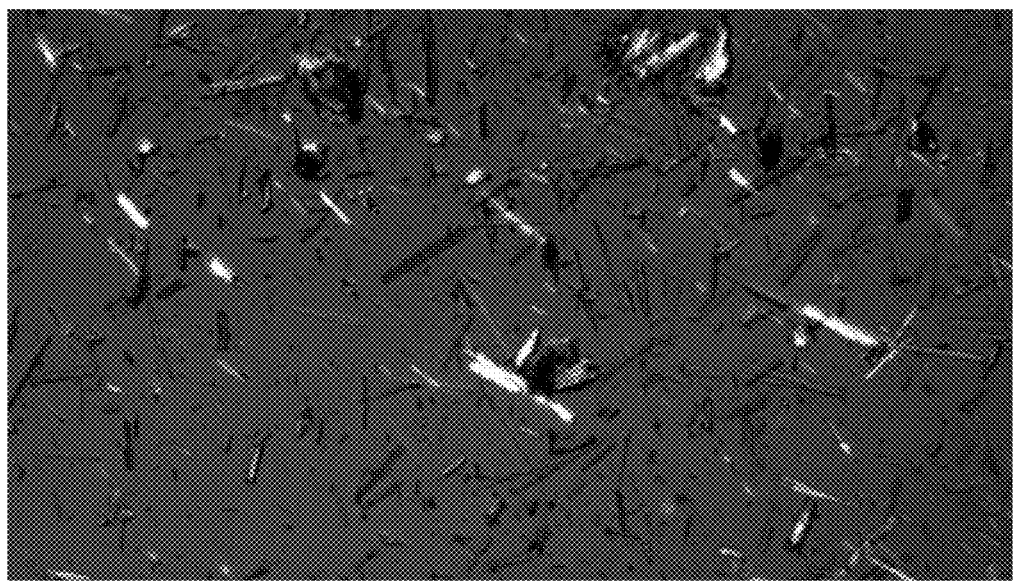
FIG. 5 is a graphical representation of the optical micrograph of crystalline Form II.
Figure 6:
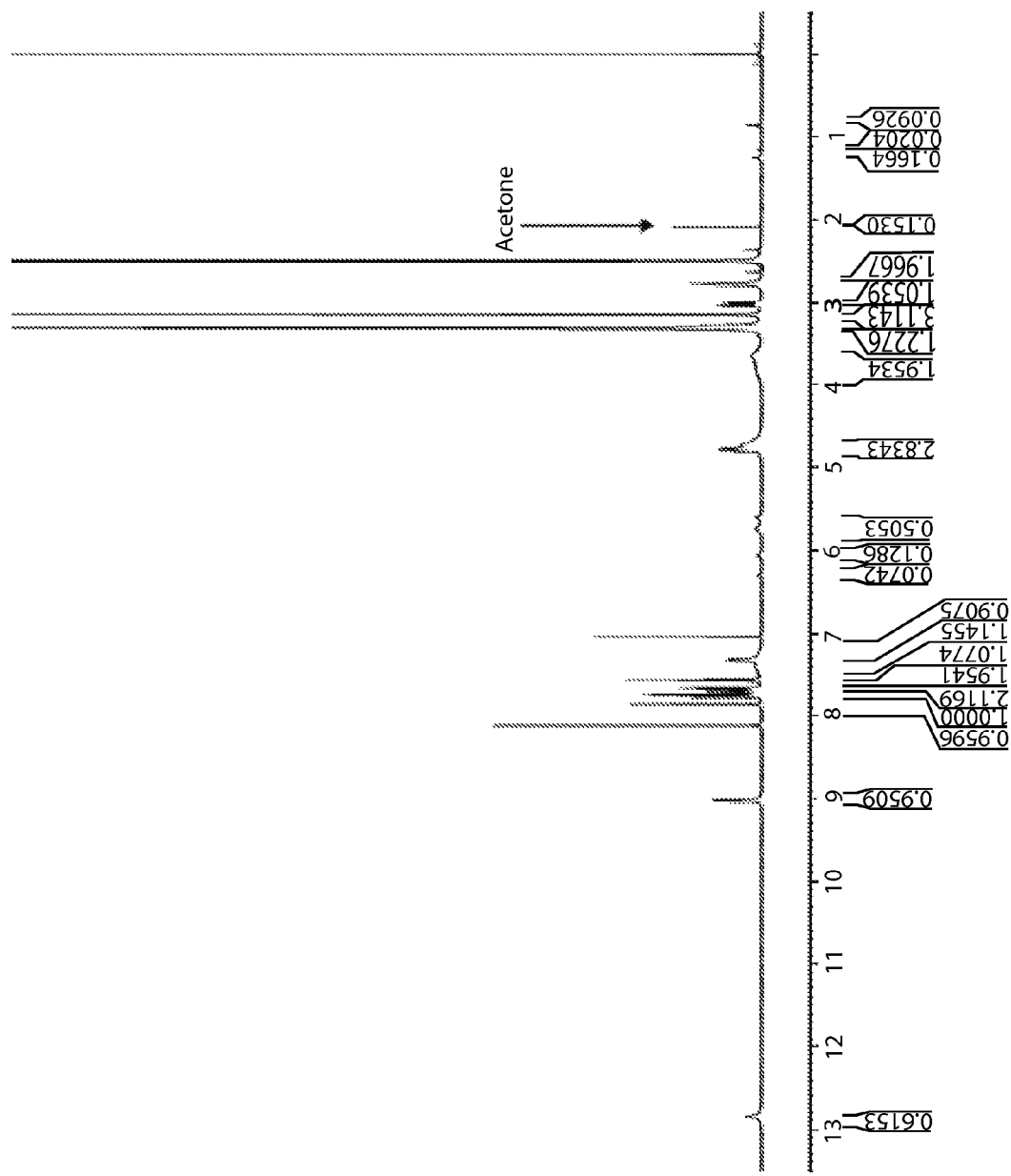
FIG. 6 is a graphical representation of the $^1$H NMR spectrum of crystalline Form II.
Figure 7:
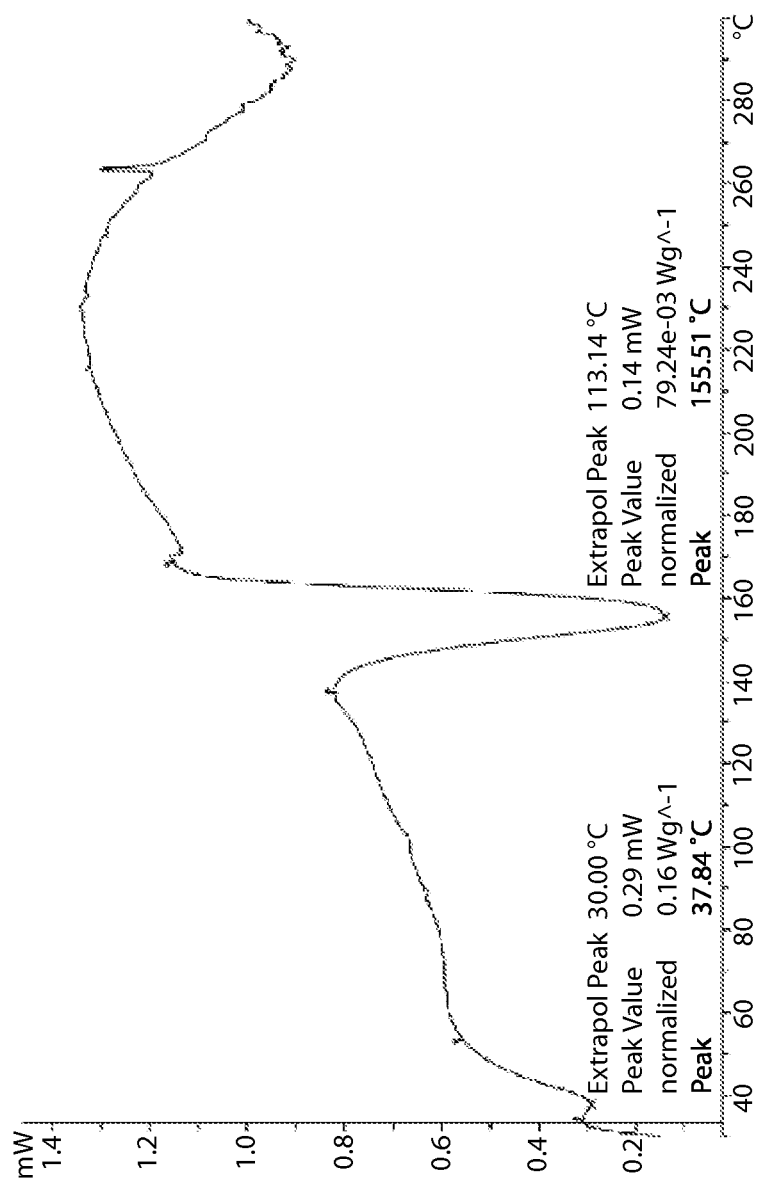
FIG. 7 is a graphical representation of the DSC thermogram of crystalline Form II.

The $^1$H-Nuclear Magnetic Resonance spectrum of crystalline Form II shown in FIG. 6 is consistent with structure of compound and contains 0.2 wt % acetone. The crystalline Form II comprises a powder x-ray diffraction pattern as shown in FIG. 4 with an acicular morphology as indicated in FIG. 5. DSC analysis of Form II shows a small endotherm at 37.8° C., likely due to loss of acetone and/or water, and a melting transition at 155.5° C. as presented in FIG. 7. The thermal events assigned in the DSC thermogram of Form II are consistent with the observations from hot stage microscopy analysis of the polymorph.

Figure 8:
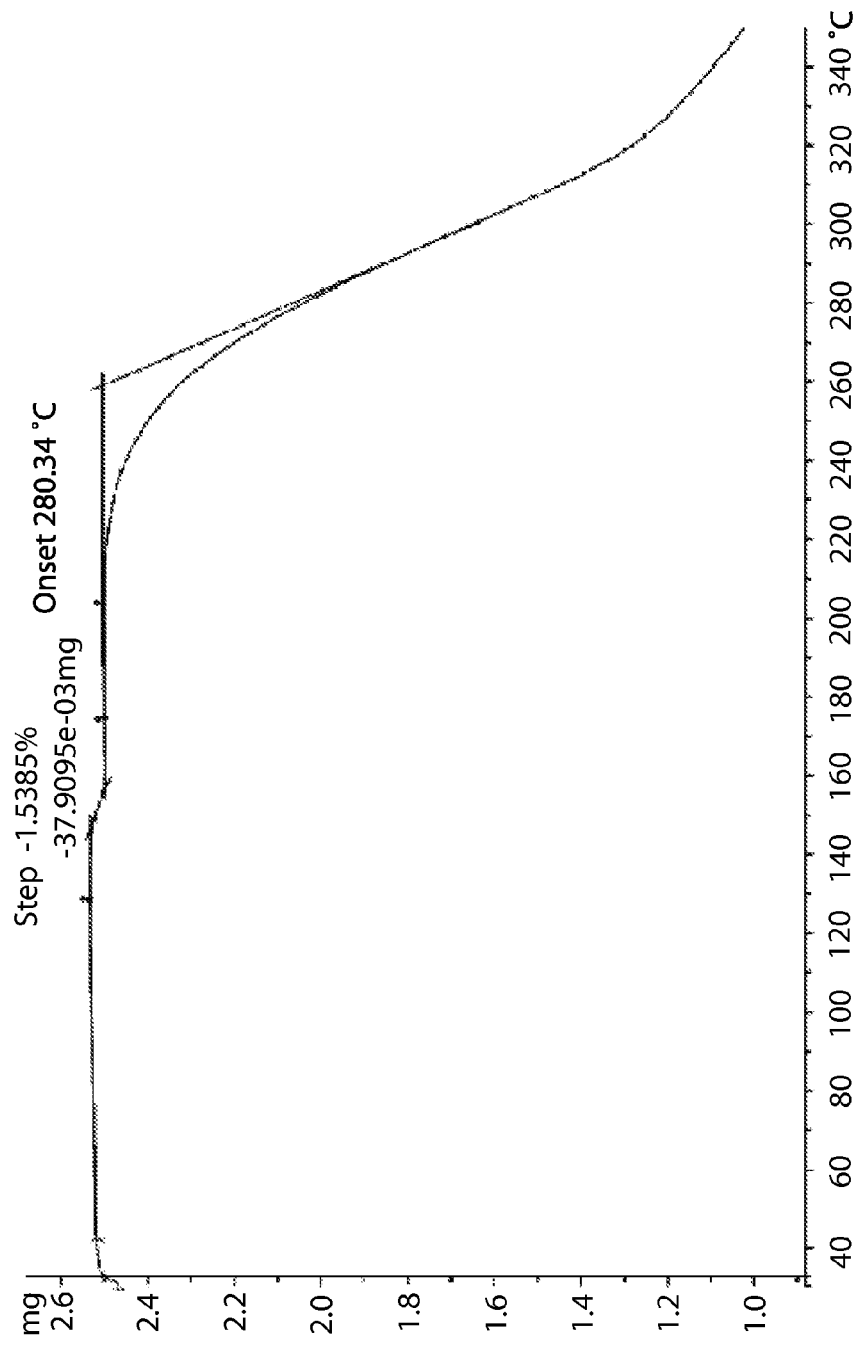
FIG. 8 is a graphical representation of the TGA thermogram of crystalline Form II.
Figure 9:
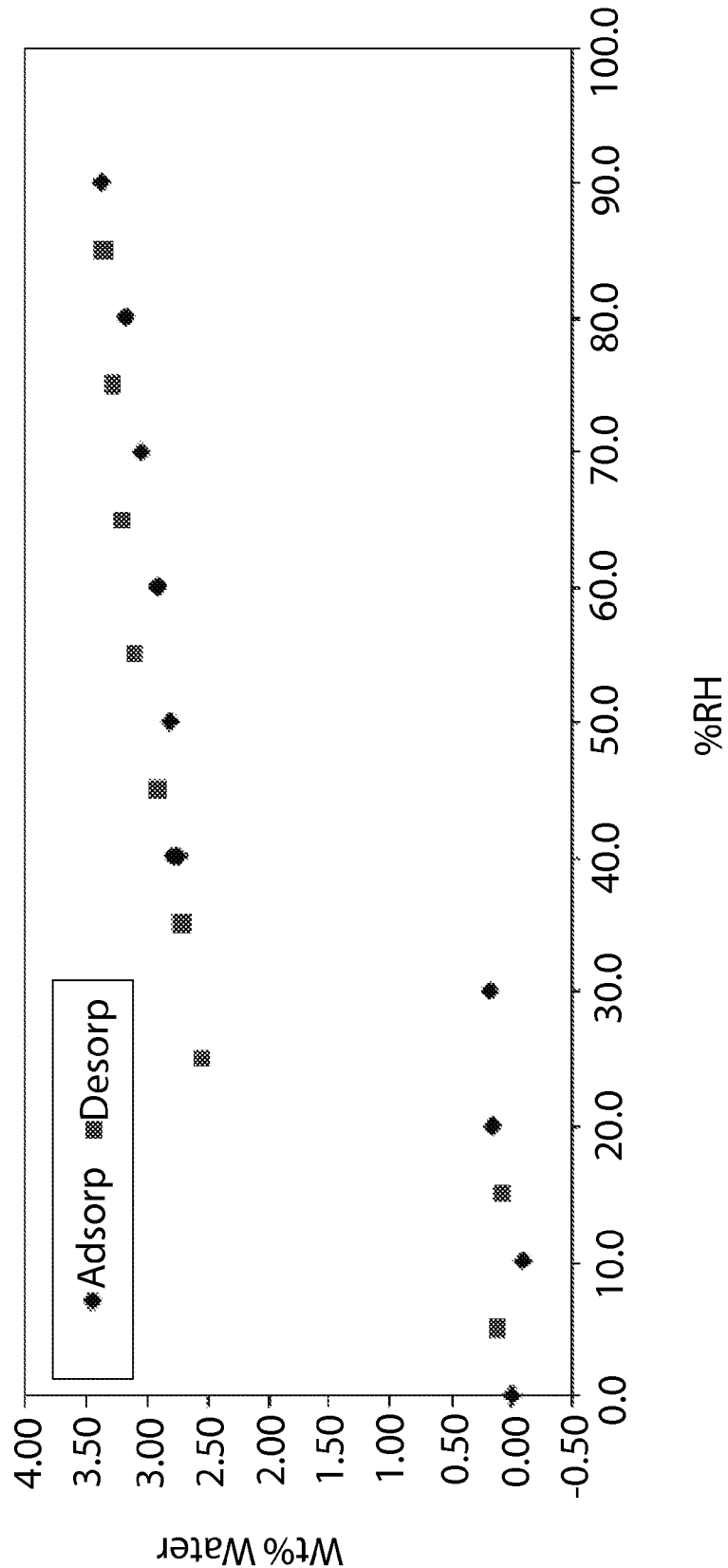
FIG. 9 is a graphical representation of gravimetric moisture sorption curve of crystalline Form II.

A thermogravimetric analysis graph of crystalline Form II is shown in FIG. 8. A mass loss of 1.5 wt %, attributed to liberation of water during the melt, followed by onset of decomposition at 260° C. is observed. Gravimetric moisture sorption analysis reveals that Form II is moderately hygroscopic, absorbing 3.0 wt % water at 60% relative humidity and 3.4 wt % water at 90% relative humidity. The water content of the Form II under 40% relative humidity is 2.8 wt %, which is close to the theoretical water content of a monohydrate of the compound (2.9 wt %). The water content of Form II by Karl Fisher titration is 3.2 wt %, again in-line with a monohydrate of compound.

While selected embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of synthesizing a compound of Formula I:

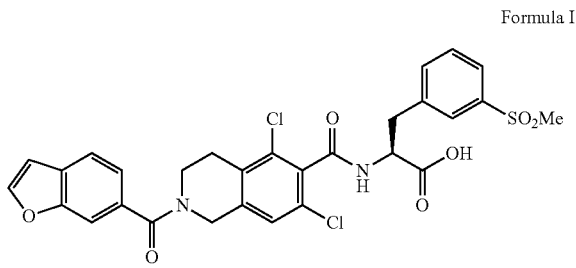 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula I or a salt thereof, comprising the steps:
 a) performing hydrolysis of Formula AA with a base under biphasic conditions:

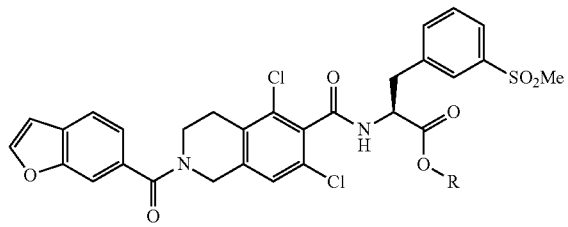

Formula AA wherein R is a carbon-containing moiety or a silyl-containing moiety; and
 b) isolating said compound of Formula I or a salt thereof.

2. The method of claim 1, wherein the biphasic conditions include aqueous acetone.

3. The method of claim 2, wherein the aqueous acetone is about 30% aqueous acetone.

4. The method of claim 2, wherein the aqueous acetone is present in an amount ranging from about 1:1 to about 5:1 by weight with respect to Formula AA.

5. The method of claim 1, wherein the base is sodium hydroxide.

6. The method of claim 5, wherein the sodium hydroxide is added in an amount ranging from about 1.0 to about 1.5 equivalents.

7. The method of claim 6, wherein the sodium hydroxide is added in an amount of about 1.2 equivalents.

8. The method of claim 1, further comprising a phase transfer catalyst.

9. The method of claim 8, wherein said phase transfer catalyst is a quaternary ammonium salt.

10. The method of claim 9, wherein said quaternary ammonium salt is tetrabutylammonium hydroxide.

11. The method of claim 8, wherein said phase transfer catalyst is present in an amount ranging from about 0.01 equivalents to about 0.5 equivalents.

12. The method of claim 1, wherein R is a substituted or unsubstituted group selected from lower alkyl, lower alkenyl, lower alkynyl, cyclo(lower)alkyl, cyclo(lower)alkenyl, aryl, aralkyl, heterocyclyl, and heteroaryl groups.

13. The method of claim 1, wherein Formula AA is:

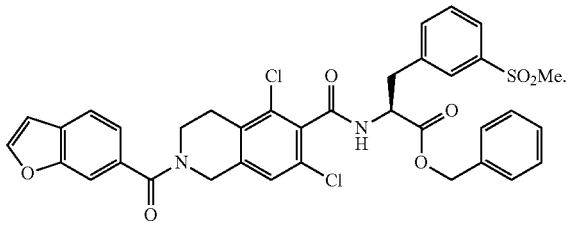

Compound 19

14. The method of claim 1, further comprising purifying said compound of Formula I by recrystallization.

15. The method of claim 14, wherein said recrystallization is performed with aqueous acetone.

16. A composition comprising a compound of Formula I:

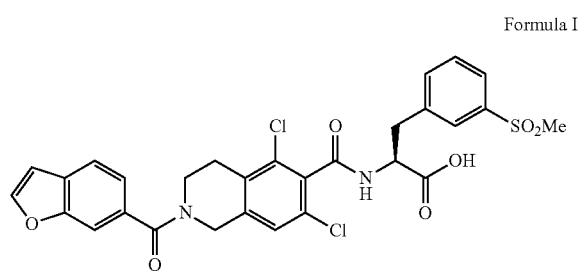 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula I wherein said compound is synthesized by a process comprising the following steps:

a) performing hydrolysis of Formula AA with a base under biphasic conditions:

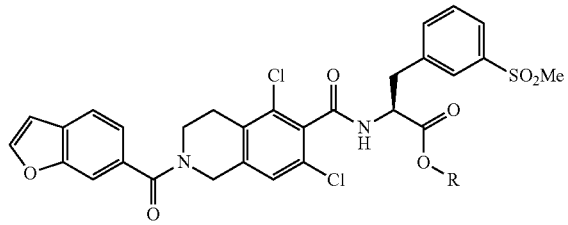

Formula AA wherein R is a carbon-containing moiety or a silyl-containing moiety; and b) isolating said compound of Formula I or a salt thereof, and further wherein said compound has an optical purity of >98%.

* * * * *